(12) United States Patent
Williams

(10) Patent No.: US 6,931,274 B2
(45) Date of Patent: *Aug. 16, 2005

(54) PROCESSING EEG SIGNALS TO PREDICT BRAIN DAMAGE

(75) Inventor: Christopher Edward Williams, Grafton (NZ)

(73) Assignee: Tru-Test Corporation Limited, Hamilton (NZ)

(*) Notice: Subject to any disclaimer, the term of this patent is extended or adjusted under 35 U.S.C. 154(b) by 0 days.

This patent is subject to a terminal disclaimer.

(21) Appl. No.: 10/140,360

(22) Filed: May 6, 2002

(65) Prior Publication Data

US 2003/0023183 A1 Jan. 30, 2003

Related U.S. Application Data

(63) Continuation-in-part of application No. 09/509,186, filed as application No. PCT/NZ98/00142 on Sep. 23, 1998, now Pat. No. 6,493,577.

(30) Foreign Application Priority Data

Sep. 23, 1997 (NZ) ............................................. 328820

(51) Int. Cl.[7] .............................................. A61B 5/00
(52) U.S. Cl. ..................................................... 600/544
(58) Field of Search ................................ 600/300, 544, 600/545

(56) References Cited

U.S. PATENT DOCUMENTS 5,309,923 A * 5/1994 Leuchter et al. ............ 600/544
6,493,577 B1 * 12/2002 Williams ..................... 600/544

* cited by examiner

*Primary Examiner*—Robert L Nasser
(74) *Attorney, Agent, or Firm*—Fliesler Meyer LLP

(57) ABSTRACT

Rapid and accurate in-vivo assessment of cerebral white matter injury particularly for pre-term infants, for timely treatment and/or prediction of outcomes has been very limited. This invention exploits the discovery that reduced high-frequency EEG intensity, particularly as shown by the upper spectral edge frequency, is a good indicator of cerebral white matter neural injury and is well correlated with MRI results. With more experience of clinical cases, a set of simple rules such as "if the spectral edge value is below 8 Hz there is a high likelihood of injury" may be validated, yet the EEG technology involved is largely invisible to the user. In the invention, EEG signals are processed by software to obtain, store, and graphically display bilaterally collected EEG spectral edge and intensity values over from hours to weeks. Rejection of corrupted signals by filtering and gating means is responsive to incoming signal characteristics, to additional inputs such as motion sensors or impedance tests, and to patient data (gestational age in particular). The invention includes the software and methods of use.

64 Claims, 15 Drawing Sheets

PROCESSING EEG SIGNALS TO PREDICT BRAIN DAMAGE

CROSS REFERENCE TO RELATED APPLICATIONS

This application is a continuation-in-part of application Ser. No. 09/509,186, filed Apr. 7, 2000, now U.S. Pat. No. 6,493,577, application Ser. No. 09/509,196 is a 371 of PCT International Application No. PCT/NZ98/00142, filed Sep. 23, 1998, which in turn claims the priority of New Zealand Application No. 328820, filed Sep. 23, 1997. Each of these applications is incorporated into this application by reference.

BACKGROUND OF THE INVENTION

1. Field of the Invention

This invention relates to a apparatus for display of a processed, condensed derivative of electroencephalographic (EEG) signals.

2. Discussion of the Related Art

Cerebral/neural injuries in pre-term infants are telatively difficult to assess and to track during their course, using skills and equipment available at the time of this application; yet intervention may be highly desirable. Magnetic resonance imaging (MRI) is the only reliable non-invasive assessment available to a neo-natal intensive care unit. MRI is limited to (a) revealing lesions in older infants, typically over 34 weeks, and (b) to showing structural correlates of changes that are already too late for intervention, it being 3–4 days before MRI scans show injury. Ultrasound imaging is significantly less reliable than MRI in this area. It has been estimated that up to 70% of cases of apparent hypoxic-ischemic injury are missed.

Very premature infants have a markedly increased risk of neurological morbidity [Volpe, Prev. Med., 23:638–645, 1994]. A recent study using cranial ultrasonography revealed that only 2% of infants born at 23 weeks, 21% at 24 weeks and 69% at 25 weeks survived without severe abnormalities [Allen et al., New Eng. J. Med., 329:1597–1601, 1993]. White matter brain damage is a characteristic of these injuries. Patterns of damage range from subtle gliosis (telencephalic leukomalacia) through to severe cystic infarctions of the periventricular and subcortical white matter [Volpe, op. cit.].

Histopathologic studies indicate some of these lesions develop prenatally, others postnatally. Poor neurological outcome is associated with the presence of these white matter injuries [Guit et al., Radiolog, 175:107–109, 1990]. Severe periventricular lesions are strongly associated with cerebral palsy [Hoon, J. Perinatol., 15:389–394, 1995].

Long term neurological outcome appears to be similarly compromised. In a group of less than 32 week old premature infants reviewed at the age of 9 years 19% were in special education, 32% were in a grade below the appropriate level for their age and 38% required special assistance [Hille et al., J Pediatr., 125:426–434, 1994]. Similarly, another study has shown that in very premature infants about 5–15% develop major spastic motor deficits and an additional 25–50% exhibit developmental and cognitive disabilities [Volpe, Biol. Neonate, 62:231–242, 1992]. The etiology of these lesions is not completely understood [Armstrong, Semin. Perinatol., 17:342–350, 1993], but they are thought to occur secondary to various prenatal environmental and genetic factors [Lou, Brain Dev., 16:423–431, 1994].

Cerebral hypoperfusion is considered to be a significant final common pathway in the pathogenesis of these encephalopathies [Lou, op. cit.]. Experimental and epidemiological studies generally support this hypothesis. For example, intrapartum acidosis and asphyxia in the premature infant carry a high risk of periventricular leukomalacia [Low et al., Am. J. Obstet. Gynecol, 162:977–981, 1990]. Also, both increased levels of hypoxanthine and prolonged metabolic acidosis in the neonatal period are associated with a high risk of periventricular lesions [Russel et al., Arch. Dis. Child., 67:388–392, 1992; Low et al., op. cit.]. In particular, periventricular lesions are probably caused by cerebral hypoxia-ischemia following arterial hypotension [Iida et al., Pediatr. Neurol., 8:205–209, 1992]. Cerebral hypoxia-ischemia may arise from problems associated with prematurity including respiratory distress syndrome, patent ductus arteriosis, necrotizing enterocolitis and sepsis. There is considerable variation in the pattern of lesions observed and a range of factors are likely to influence outcome, including gestational age and the severity and nature of the insult [Gluckman et al., "Proceedings of the Alfred Benzon Symposium No. 37, Munksgaard, Copenhagen, 1993. ]Other factors such as hypoglycemia, infections or toxemia are also likely to be important [Piekkala et al:, Early Hum. Dev., 13:249–268, 1986].

Current methods for assessing brain injury reveal damaged areas of the brain, but do not identify those premature infants at risk of suffering a neural injury. Brain damage assessed by neurological examination is of limited prognostic value, especially for those pre-term infants on life support. Ultrasonography is also used and reveals lesions as white matter echodensities and echolucencies, which are useful in predicting future handicap, such as cerebral palsy. However, this approach is less suitable for monitoring and detecting pathophysiologic events which may occur over several days, the knowledge of which could be used to minimize or avoid further injury. Greater reliance needs to be placed on other investigations such as pathophysiologic measures [Hill, Clin. Invest. Med., 16:141–148, 1993]. Doppler cerebral hemodynamic measures have not been proven to be predictive of outcome [Shortland et al., J. Perinat. Med., 18:411–417, 1990]. In the more mature brain the EEG signal can be used to predict severe loss of the superficial neurons that generate this signal [Williams et al., Ann. Neurol., 31:14–21,1992].

Two patterns of white matter damage can occur: "subtle" white-matter damage which manifests as gliosis, impaired myelination, and ventriculomegaly, and is often termed telencephalic leukomalacia; and "severe" cystic infarctions within the periventricular and subcortical white matter. The former lesions are associated with cognitive deficits and the latter are strongly associated with cerebral palsy.

Histopathological studies indicate the timing of injury is variable—some injuries may develop prenatally whereas many others appear to develop during the first postnatal weeks. However in surviving infants the timing of injuries is typically unclear and there are considerable problems with detecting when these white matter injuries occur [Murphy et al., Arch. Dis. Child Fetal Neonat. Ed., 75(1 Special Issue SI):F 27–F32, 1996]. The inability to detect the onset of injury makes management difficult. For example, if a subtle or severe injury to the deep white matter could be rapidly detected, then the injurious factor could be corrected or treatment applied. The use of EEG-related parameters is believed to closely reflect the development of subtle or severe injury and consequent brain lesions within white matter (tracts) and/or gray matter (neuron bodies).

The appearance of positive Rolandic sharp waves (PRSW) in an EEG has been found to be specific for some cases, but to give false negative results in as many as 70% of extremely low birth weight infants even if it is done by a person experienced in interpreting EEG traces. One problem to be solved is to provide a more sensitive test than one relying on the PRSW, so that at least some types of brain injury can be recognized, their severity and coverage may be quantified and their effects may be alleviated by timely intervention. Many such lesions (though not all, given the brain's ability to compensate) will manifest themselves as adverse outcomes by about 18 months of age and an ability to predict such outcomes is desired.

It is evident from the above that there is a need for a device capable of reporting accurately on the current level of a pre-term infant's neural status; to be useful in prediction of outcomes and to lead to a considerable improvement in the treatment of infants with, or likely to develop, white matter neural injury. The inventor's group is already active in this area (see, for example, WO 00/13650). After working with a fetal sheep model, the inventor has constructed a Brain Rescue Monitor (see, for example, U.S. Pat. No. 5,807,270 and WO 98/57139), using EEG-type skin electrodes to collect signals for processing in the frequency domain, and to make real-time displays of trends of neural status occurring over periods of time from minutes to weeks.

Related to long-term EEG-based recordings, a further problem remaining to be solved is to reliably and consistently recover, over an extended period of perhaps 6 hours to a week, and in a non-ideal space, the very weak signal that comprises a typical EEG. This signal is easily corrupted by intrinsic noise and external interference. The BRM is suitable for long-term, semi-automatic monitoring of neural function although the lack of direct, continuous human supervision over signal quality imposes a particular requirement for effective rejection of artifacts inadvertently included with the data. At the same time, a real pathophysiological change, likely to influence treatment, must not be altered by any filtering procedure.

SUMMARY OF THE INVENTION

The invention provides an apparatus (a brain rescue monitor or BRM) and method for detecting white matter neural injury and predicting neurological outcome, in subjects, particularly in pre-term infants.

In broad terms, the invention is apparatus by means of which EEG signals may be acquired from a subject, filtered and verified for quality, and then analyzed particularly in relation to frequency distribution in order to produce output information indicative of cerebtal white-matter neural injury within the brain of, and likely outcome for the subject.

Thus, this invention includes an apparatus for processing an electroencephalogram (EEG) signal from a subject to assist in management of possible cerebral white-matter neural injury in the subject, comprising:
(a) apparatus to acquire at least one channel of an EEG signal from the subject over a period of time, and
(b) computing apparatus programmed to analyze the frequency distribution of the intensity within the EEG signal so acquired, from within a range of from 1 Hz to 50 Hz, and to produce condensed output information descriptive and/or predictive of cerebral white-matter neural injury in the subject.

In a second aspect, this invention is a method for detecting white matter neural injury and predicting neurological outcome for a patient, comprising: acquiring an EEG signal from the subject, and analyzing the frequency distribution of the signal(s) to produce output information indicative of cerebral white-matter neural injury for the subject.

Preferably the method includes collection of the analyzed signals and related neurological and clinical information to produce information useful for managing the subject and preferably for also predicting an outcome.

In a third aspect, this invention is software for use in the apparatus and method of the first two aspects of this invention.

BRIEF DESCRIPTION OF THE DRAWINGS

FIG. 3a is a recording from a normal infant and FIG. 3b is a recording from an infant with cystic white-matter lesions.

DETAILED DESCRIPTION OF THE INVENTION

Definitions

Figure 1:
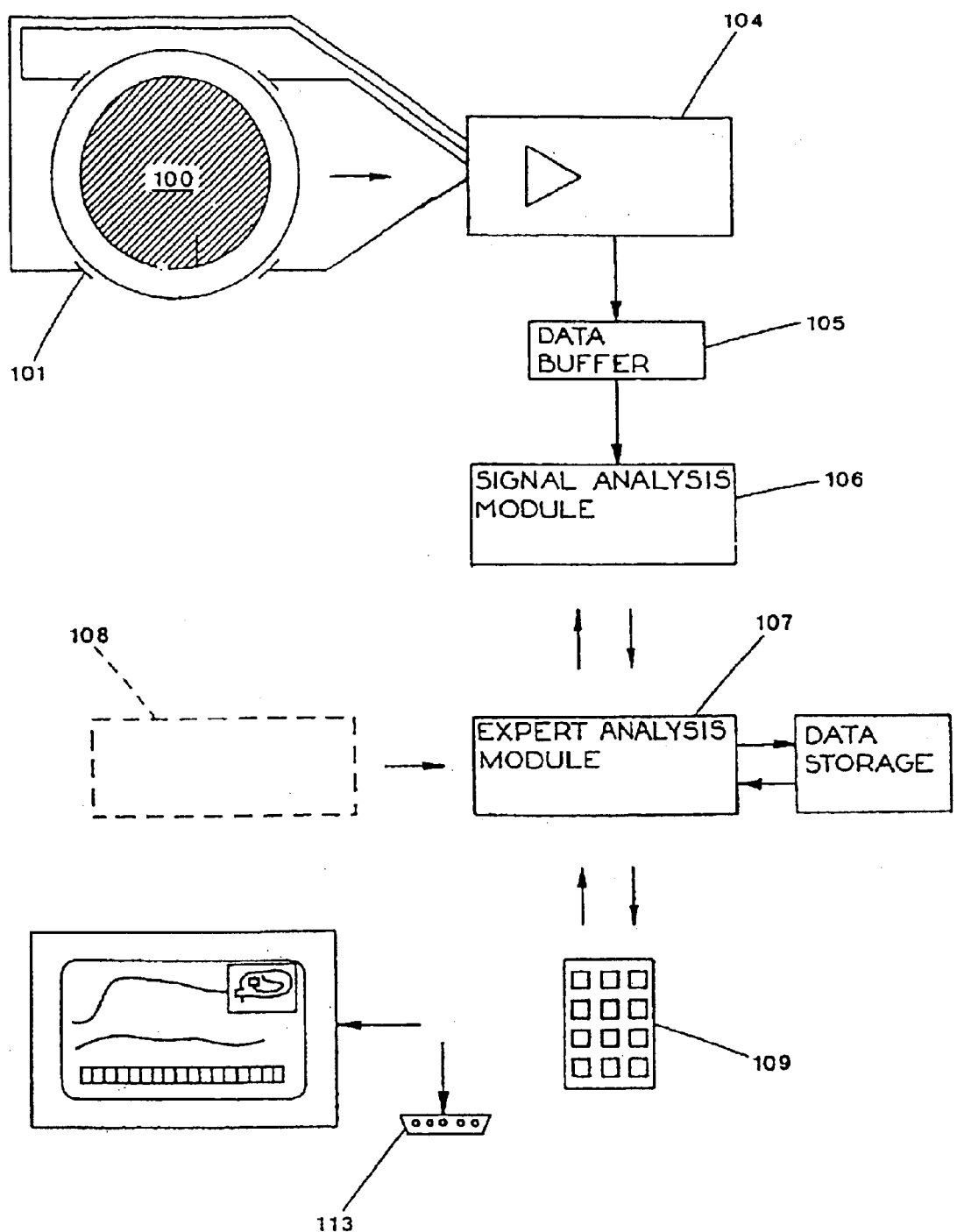
FIG. 1 is an overview of one form of the apparatus of the invention.

An "electroencephalogram" or "EEG" comprises an outward indication of electrical activity from the most superficial layers of the cerebral cortex, usually recorded from electrodes on the scalp. This activity is the result of the rhythmic discharging of neurons under the electrode. The EEG signal provides information about the frequency and amplitude of the neuronal electrical activity and its temporal variation.

The "spectral edge frequency" is the xth percentile frequency of the EEG intensity over the frequency band 2 Hz to 20 Hz, i.e. the frequency below which lies x % of the total EEG intensity. Unless another percentile is specifically referred to, the "spectral edge frequency" is the 90th percentile frequency (more correctly "upper decile cortical spectral edge frequency"), and is the 90th percentile frequency of the EEG intensity over the frequency band 2 Hz to 20 Hz, i.e. the frequency below which lies 90% of the total EEG intensity.

"EEG intensity", "EEG amplitude", and "EEG power" are closely related measurements for the magnitude of brain electrical activity. The terms "EEG intensity" or just "intensity" will be used in this application.

The "total EEG intensity" (usually expressed in $\mu V^2$ is the sum of the power spectrum between 2 Hz and 20 Hz.

Description

This invention provides method and apparatus to make use of the discovery that a lowering of the frequency distribution of the EEG activity, as measured by a fall in spectral edge frequency of the EEG signals, is indicative of cerebral white matter injury. Typically the EEG frequency spectrum comprises signals in a 2 to 20 Hz range, with most activity between about 2 and 15 Hz. Alternatively, signals in a 1–35 Hz range may be used. In the method and system of the invention, the EEG signals are analyzed to determine the proportion of the power spectrum in the top 50%, preferably the top 30%, more preferably the top 10%, and perhaps even just the top 5% of the frequency range, and a reduction in this spectral edge frequency is indicative of cerebral white matter both subtle and severe white matter injuries and long term neurological outcome.

In the method and system of the invention a suitable conventional electrode, amplifier and patient isolation system is used to acquire at least one EEG signal from the head of a subject such as an infant, especially a pre-term infant, which are then analyzed in apparatus comprising signal analysis software arranged to examine the upper portions or spectral edge of the frequency domain of the EEG signals, and to output the analysis as information indicative of neural injury and neurological outcome for the subject infant.

The system hardware may take any suitable form such as a personal computer including a dedicated data acquisition board to which one or more EEG electrodes are connected, the computer screen displaying the analysis graphically and/or as text. In another form an otherwise conventional EEG system may be arranged to process acquired EEG signals and analyze the signals according to the method of the invention, as a signal processing option on the EEG machine, and display and/or print the results. In a further form a system of the invention may comprise a smaller dedicated apparatus or instrument including EEG signal acquisition equipment, a computer section comprising an embedded microprocessor, data analysis software, and a display. In each case the results of the analysis may be displayed or printed for interpretation by a physician, or may be further processed against stored comparative information and displayed or printed in a form which is predictive of neurological outcome of the subject.

FIG. 1 schematically illustrates one form of system of the invention. A set of EEG leads are applied to the head 100 of an infant as shown at 101. The EEG signals are filtered as necessary, amplified, and analog-to-digital converted in block 104 and passed to data buffer 105. The digitized input signals data may also be compressed and stored. Data compression may involve averaging or time-to-frequency domain conversion. Standard computer-compatible data storage devices with a standard system for file naming and configuration may be utilized.

The power spectrum of the EEG signals in the frequency domain is obtained using fast Fourier transform techniques (FFT) or any other signal processing technique which enables the frequency content of the EEG signals to be extracted and the frequency distribution such as spectral edge frequency to be calculated. The preferred system is arranged to carry out this analysis in the signal analysis module 106. The results may then be displayed for interpretation by a physician, but preferably the current and stored data for the patient may be analyzed against stored comparative information on spectral edge frequency versus likely neurological outcome and analytical rules indicated by block 108, in expert analysis module 107 and the results displayed. Signal quality maintenance measures are described below.

Optionally the system may make available expert advice having an inbuilt ability to predict outcome and/or to identify the pathological processes taking place through an advisor/help system. The system may also make available representative examples of pathophysiologic reactions which can be called up by a user contemplating the case under study.

FIG. 1 also comprises a dataflow diagram and illustrates that digital signals are fed continuously into input data buffer 105, subsequently through the signal analysis module 106, and then through the expert analysis module 107, and to the display, or data storage device(s). The signal analysis module also performs artifact rejection and data reduction.

User interaction with and control of the system in the preferred form may be via a touch sensitive screen or a touch panel or keypad 109, on the front face of an instrument for example, a keyboard and/or a mouse, a separate hand held infra-red unit, or other convenient form of input device. The unit may include a printer port 113 or a built-in printer, or a network interface. Preferably the system is capable of storing and recalling data over a period of for example 3 days or more.

Preferably the system monitors each signal line in order to confirm that each channel continues to provide reliable results because (for example) attached electrodes can be detached or lose effectiveness in other ways. In the event of a problem the corresponding data is disregarded and a warning message is generated, and the system may also indicate to the user any detached or ineffective electrode.

Figure 2:
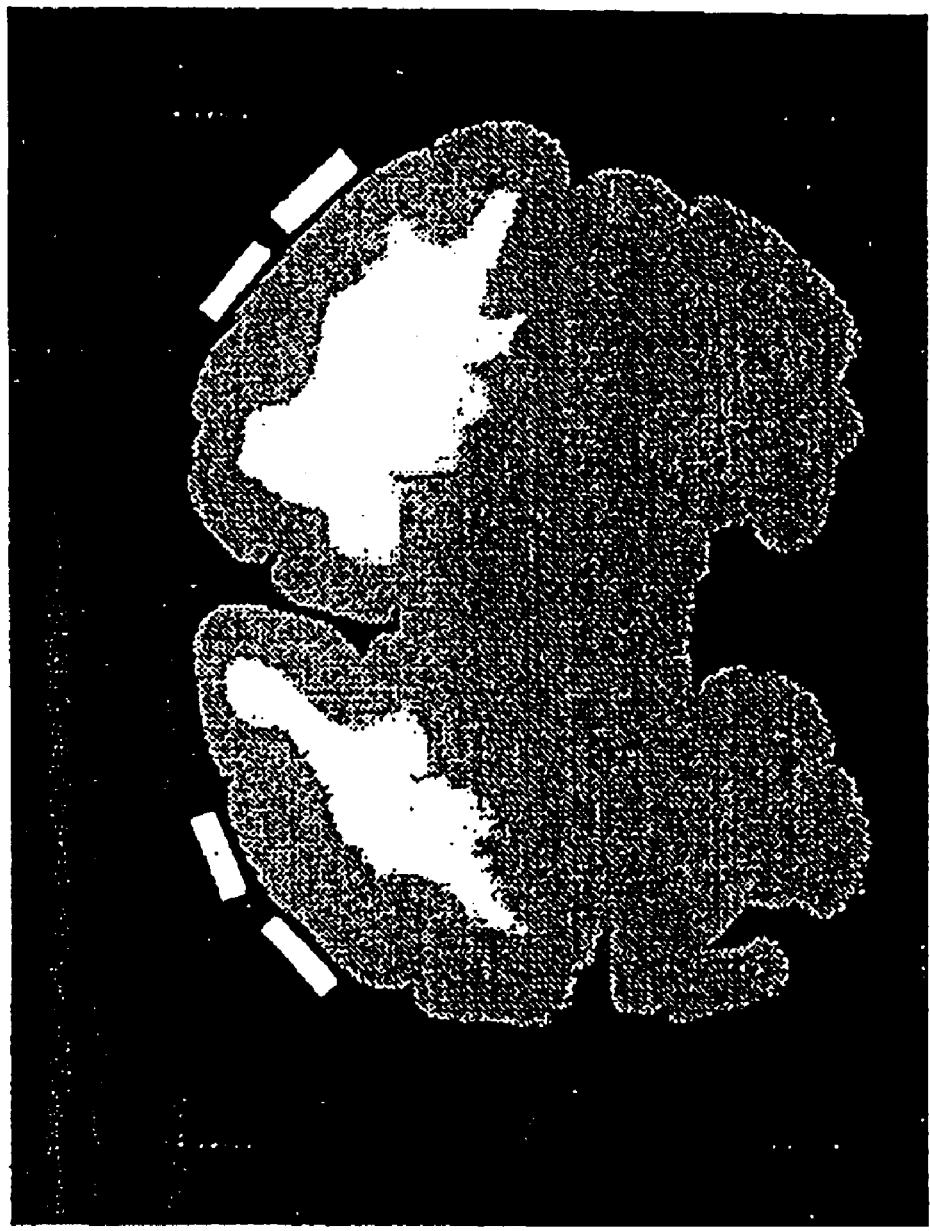
FIG. 2 is a schematic horizontal cross-sectional diagram of the brain showing where white matter injuries develop and the optimum placement of the EEG electrodes on each hemisphere for the detection of these injuries.

FIG. 2 is a schematic horizontal cross-sectional diagram of a pre-term infant's brain showing the vulnerable developing white matter regions dorsal and lateral to the lateral ventricles. These regions may suffer "subtle" injuries where gliosis occurs or develop more severe cystic lesions. Note that the overlying gray matter or neurons are typically spared from these injuries. FIG. 2 also shows the preferred EEG electrode placement with the system and method of the invention. A useful site is to record from the parasagittal region/fronto-parietal-occipital cortex that overlies the region where the white matter injury may develop as indicated in FIG. 2.

Figure 3A:
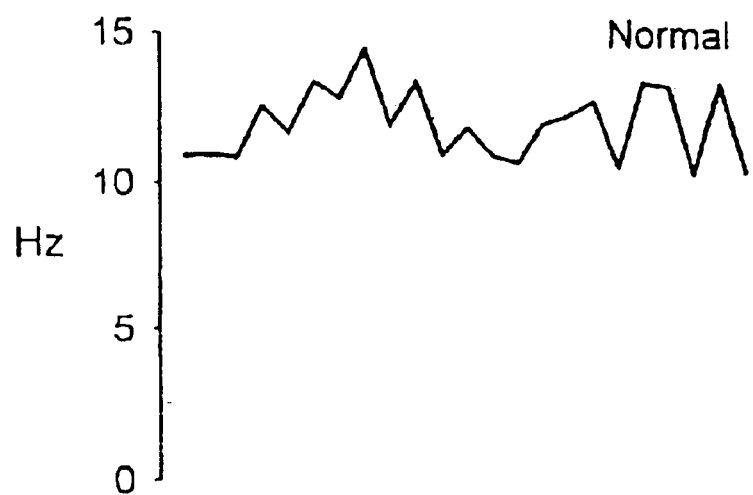
FIGS. 3a and 3b are graphs of EEG spectral edge frequency recordings for human infants.
Figure 3B:
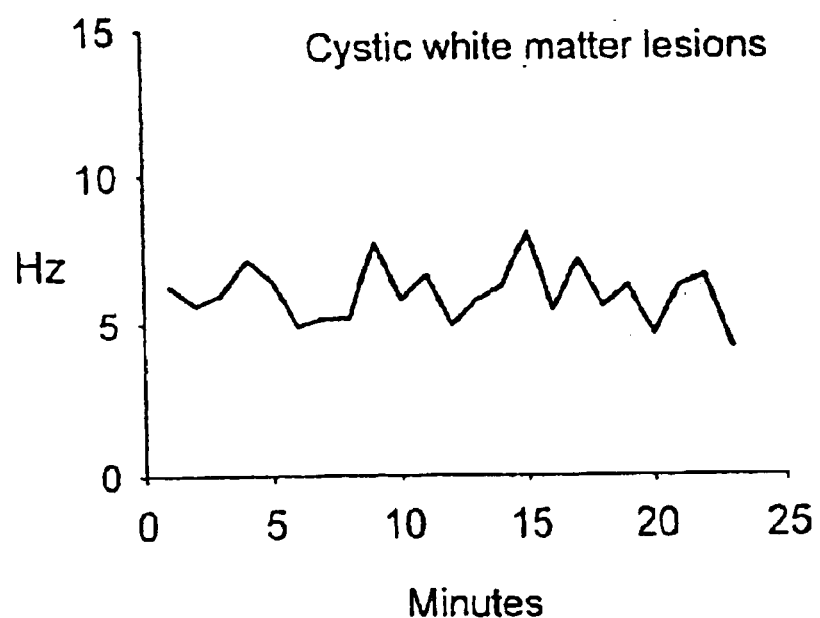

FIG. 3a shows EEG spectral edge recording for a normal human infant, with EEG activity up to about 15 Hz. FIG. 3b shows EEG spectral edge recording for an infant with cerebral white matter cystic lesions, in which there was a loss of frequency with spectral edge activity above about 10 Hz. These distinctive frequency tesponses are similar to those that were observed in the pre-term fetal sheep.

Figure 4A:
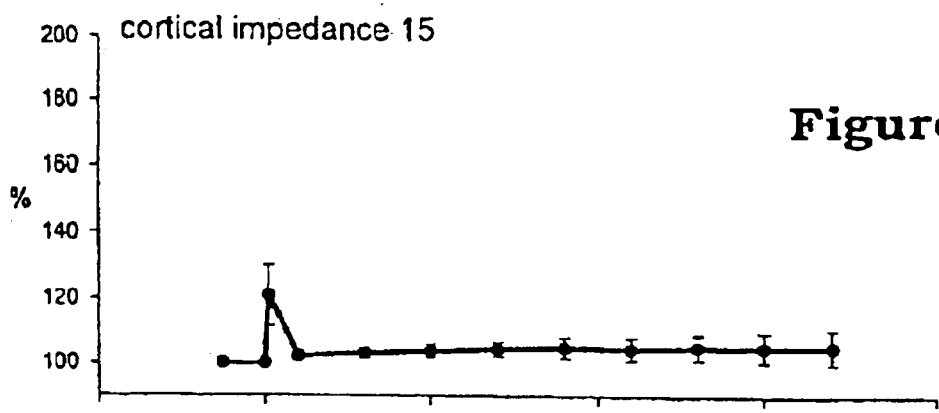
FIGS. 4a, 4b, and 4c are graphs of cortical impedance for pre-term (0.65 gestation) fetal sheep over an 80 hour period following a 15 minute (FIG. 4a), 22.5 minute (FIG. 4b), and 30 minute (FIG. 4c) cerebral hypoperfusion injury.
Figure 5A:
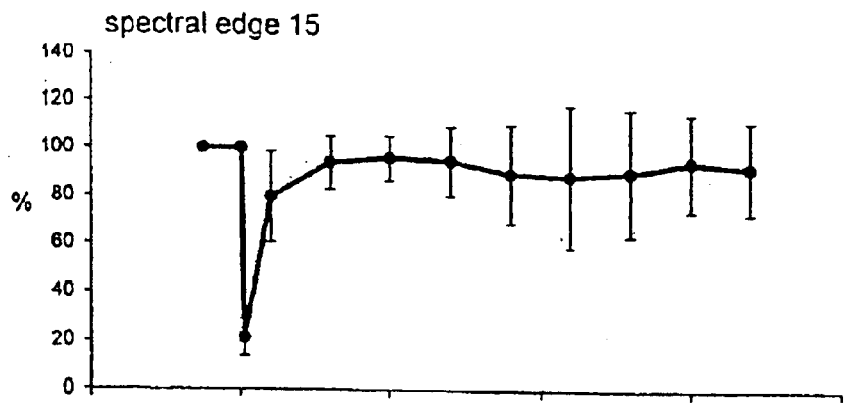
FIGS. 5a, 5b, and 5c are graphs of EEG spectral edge frequency over the same 80 hour period as FIGS. 4a, 4b, and 4c.
Figure 7A:
FIGS. 7a, 7b and 7c are graphs of the cortical impedance, EEG intensity, and spectral edge frequency from FIGS. 4a to 4c, 6a to 6c, and 5a to 5c, replotted on the same axes, showing that the distinctive spectral edge frequency response can be used to detect subtle (22.5 minutes) and severe (30 minutes) white-matter injuries. In these Figures, the closed circles represent 15 minute injury, the open circles represent 22.5 minute injury, and the closed triangles represent 30 minute injury.
Figure 7B:
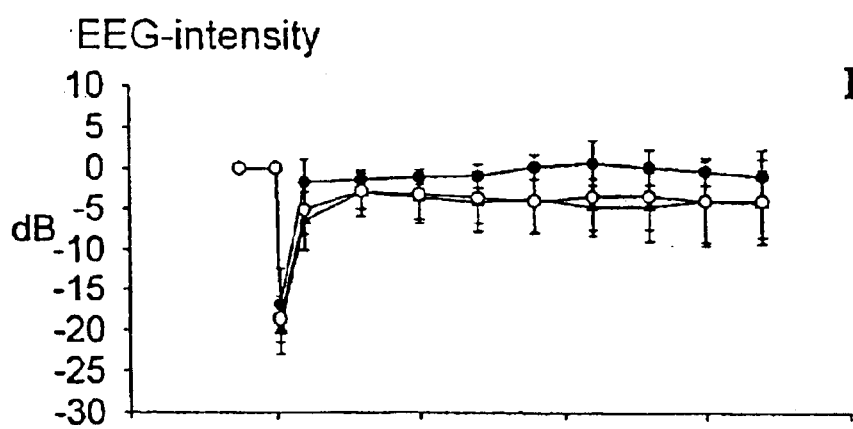
Figure 7C:
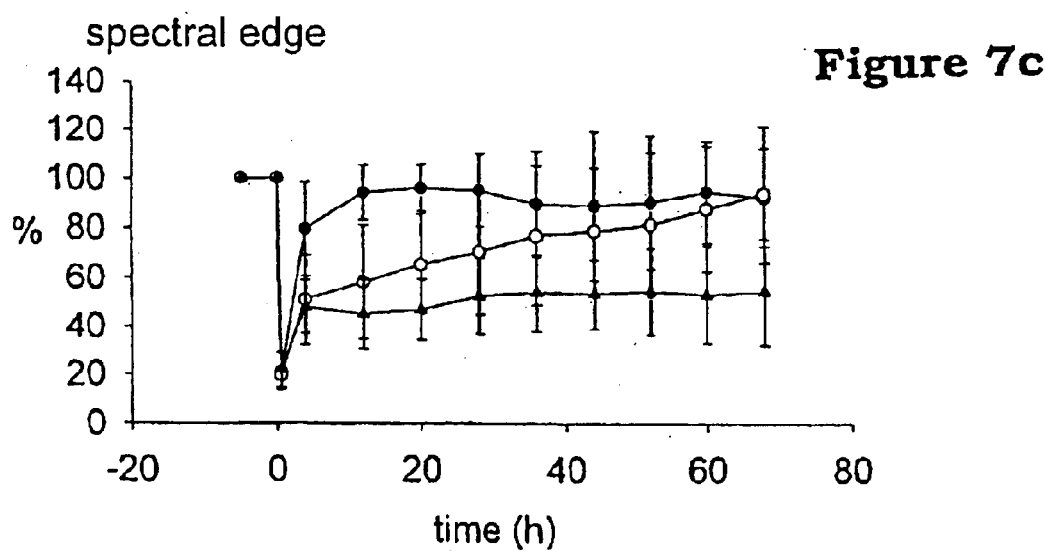

In order to determine if any biophysical parameters were useful for detecting injuries within the immature white matter the following investigations were performed. Preterm 0.65 gestation fetal sheep were subjected to cerebral hypoperfusion injury for 15, 22.5 and 30 minutes. The cortical EEG and impedance of the fetal sheep was continuously recorded and the white matter analyzed by histopathological methods for the presence of injury. At this gestational age, neurogenesis is largely complete (Patterson et al, *J. Neurochem.*, 18:2027–2040, 1971), and the cerebral sulci begin to develop: in man, this occurs between 26 and 28 weeks. The cortical component of auditory and somatosensory evoked response becomes detectable at around 0.7 gestation, whereas in man this occurs approximately 28 weeks of gestation (Hrbek et al., *Pediatr. Res.*, 8:58–63, 1974; Cook et al., *J. Dev. Physiol.*, 9:429–440, 1987; Cook et al., *J. Dev. Physiol.*, 9:441–456, 1987). Thus in terms of neural maturation the 0.65 gestation fetal sheep is highly comparable to the human between 24 and 32 weeks of gestation. During the 15-minute cerebral hypoperfusion injury, an acute rise in cortical impedance (a measure of cytotoxic edema) was measured, and a loss of spectral edge frequency in the EEG signal was observed, as seen in FIGS. 4a, 5a, and 7. In FIG. 5, 100% on the vertical axis represents normal spectral edge frequency and amplitude. These features rapidly resolved after the hypoperfusion injury.

Figure 4B:
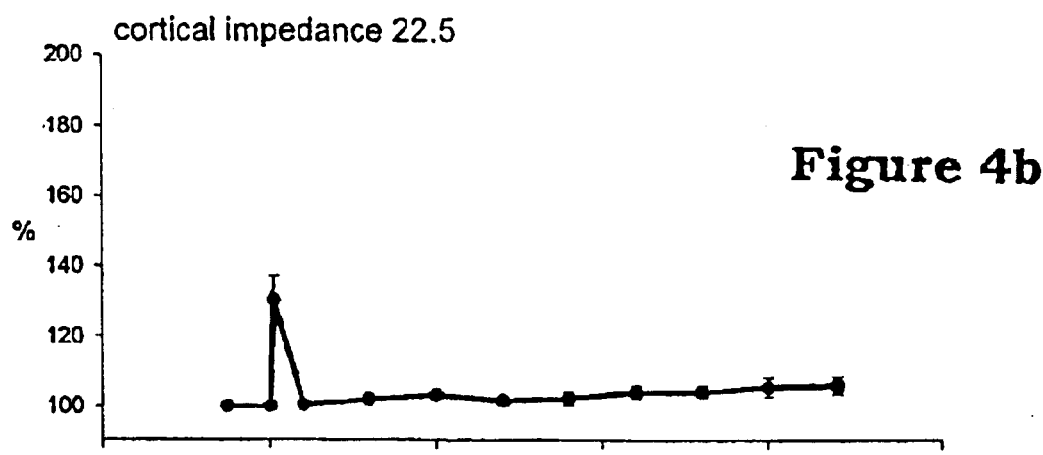
Figure 5B:
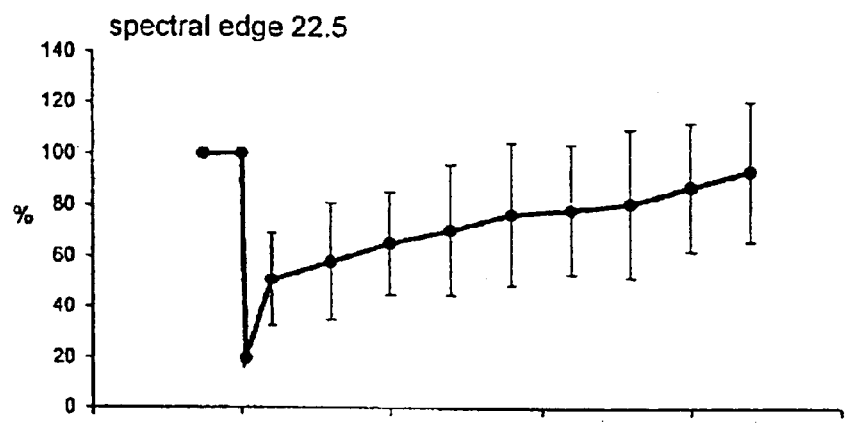

Following the 22.5 minute injury, there was a prolonged decrease in EEG spectral edge frequency, as seen in FIGS. 4b, 5b, and 7. Subsequently, histopathologic analysis of the brain material showed gliosis in the corpus callosum and subcortical white matter which extended from the periventricular region dorsally and laterally. An equivalent type of "subtle" injury is found in human infants, called telencephalic leukomalacia. The neurological outcome from this type of injury in humans is poor (Fujii et al., *Pediatr Neurol.*, 9:194–197, 1993). We believe that this loss of EEG spectral edge frequency is indicative of white matter injury.

Figure 4C:
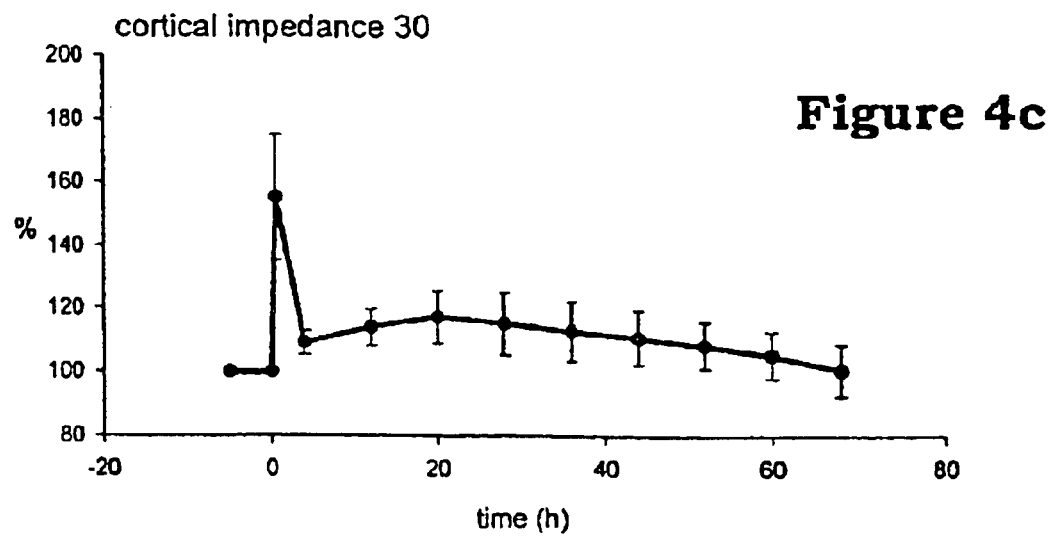
Figure 5C:
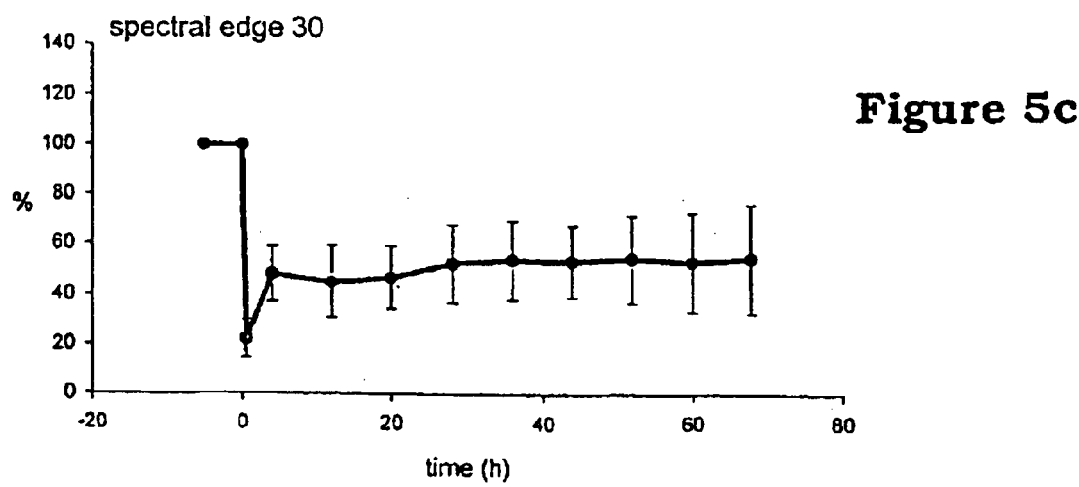

Following the 30 minute injury, a secondary rise in impedance occurred with nonrecovery of spectral edge associated with severe white matter cystic infarction, as seen in FIGS. 4c, 5c, and 7. Spectral edge activity in the EEG signal was permanently reduced to only around 50% of normal, as seen in FIG. 5c. We believe this long term loss of spectral edge frequency is indicative of low long term neurological outcome. The term given to the equivalent type of white matter injury in the human infants is periventricular leukomalacia.

Figure 6A:
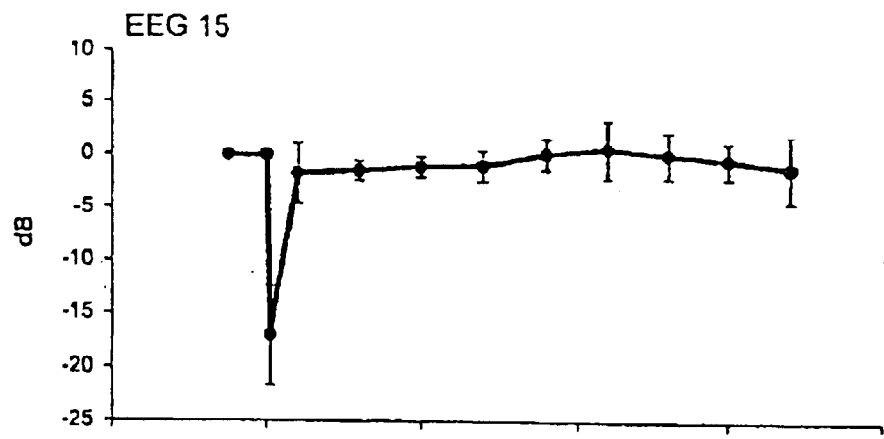
FIGS. 6a, 6b and 6c are graphs of EEG intensity over the same 80 hour period as FIGS. 4a, 4b, and 4c.
Figure 6B:
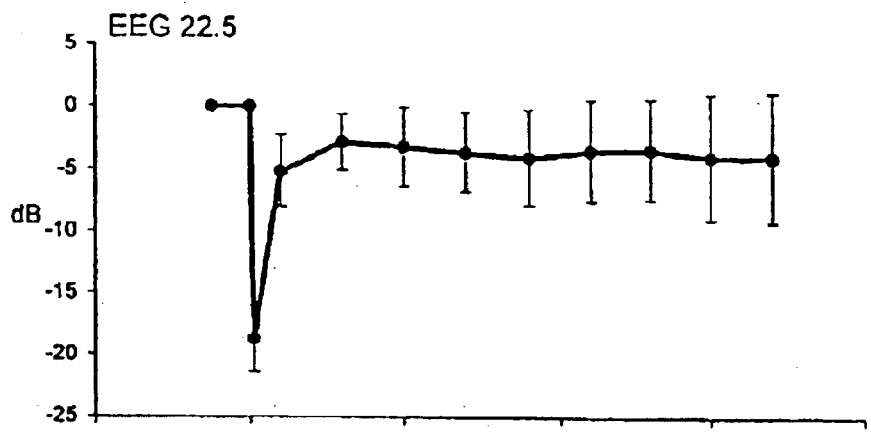
Figure 6C:
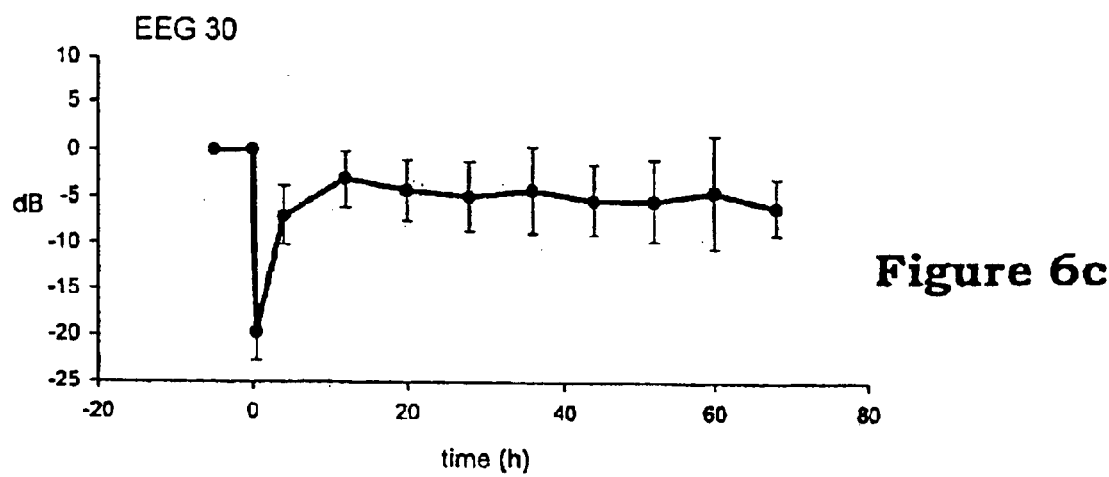

FIGS. 6a, 6b, and 6c show a transient loss of EEG intensity in each case. At the onset of diminished blood perfusion there was a rapid loss of EEG intensity and, while the recovery time to return to pre-injury EEG intensity was longer in the 30 minute injury compared with the 15 minute injury, the final outcome for the 3 durations of injury was the same.

FIG. 7 clearly demonstrates that both white matter gliosis and cystic infarction was associated with a prolonged loss of EEG frequency as indicated by the spectral edge data. In contrast the measures of the intensity (or similar measures such as power or amplitude) of the EEG were much less useful for detecting these white matter injuries following an insult.

Figure 8:
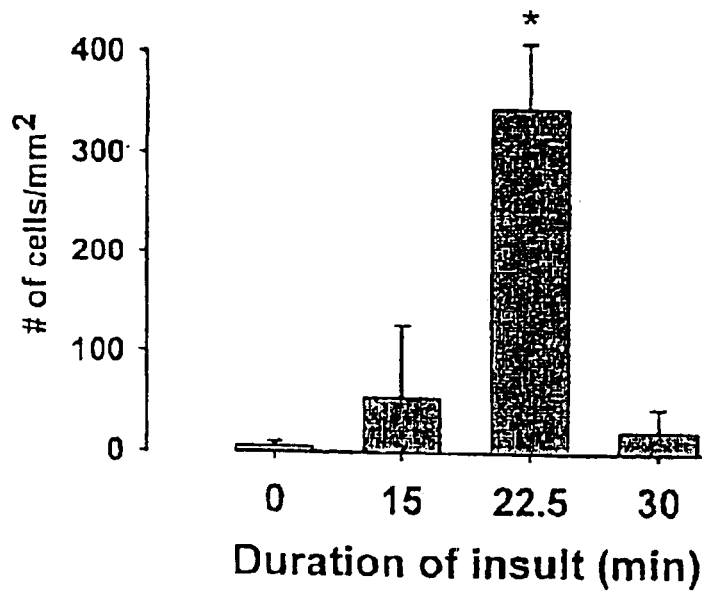
FIG. 8 is a graph comparing the density of GFAP positive cells in the subcortical white matter following different durations of ischemic injury.

FIG. 8 is a graph comparing the density of GFAP positive cells in the subcortical white matter following different durations of ischemic injury. The density of these cells was determined in the frontoparietal cortex dorsolateral to the external angle of the lateral ventricle. There was only a mild (non-significant) response in the 15 minute group. There was a marked increase in the number of GFAP positive cells in the 22.5 minute group ($p<0.05$). After the 30 minute injury, the GFAP response was less than the 22.5 minute group. This lesser induction in the 30 minute group reflects the presence of extensive cell death within the same region. (Kruskal-Wallis ANOVA on ranks). The marked increase in the number of cells (GFAP) after the 22.5 minute injury is indicative of a "subtle" injury to the white matter tracts.

Figure 9:
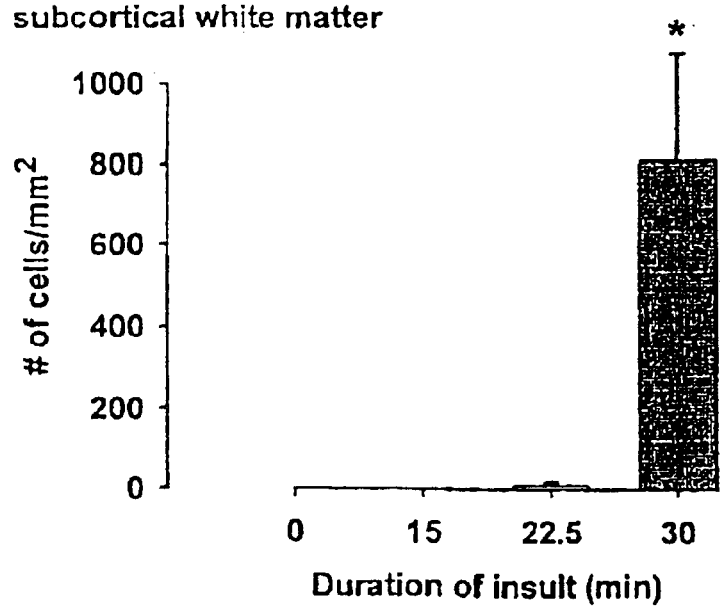
FIG. 9 is a graph comparing the density of TUNEL positive cells in the subcortical white matter following the same different durations of ischemic injury.

FIG. 9 is a graph comparing the density of TUNEL positive cells in the subcortical white matter following the different durations of ischemic injury. The density of these cells was determined in the region dorsal and lateral to the external angle of the lateral ventricle. There was a significant increase of TUNEL positive cells only after the 30 minute injury. This cell loss reflects the development of a severe or cystic white matter lesion.

Figure 10A:
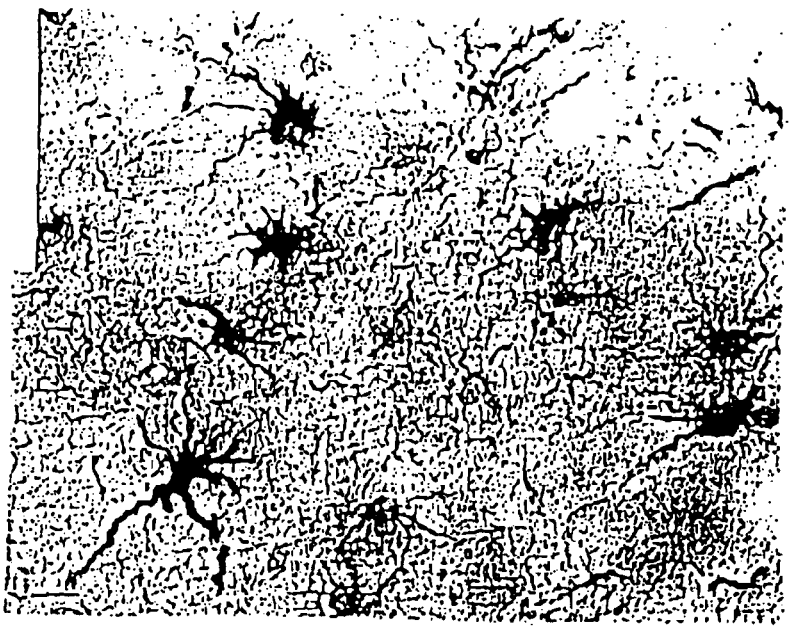
FIGS. 10a and 10b are illustrations of the diffuse glial (GFAP) reaction in the white matter of the parietal cortex following 22.5 minutes of ischemic injury and from an age matched control, respectively.
Figure 10B:
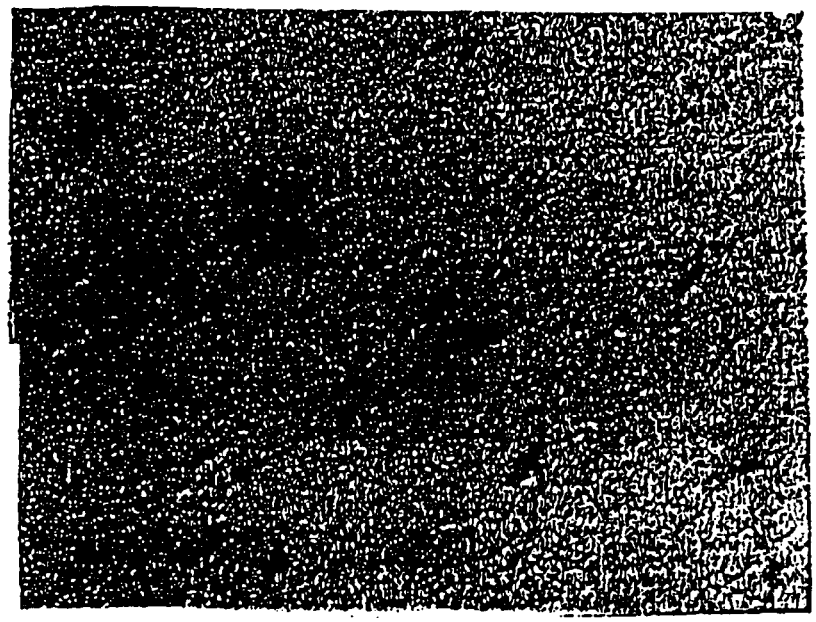

FIGS. 10 and 10b are illustrations of representative examples of the diffuse glial (GFAP) reaction in the white matter of the parietal cortex following a 22.5 minute ischemic injury and from an age matched control, respectively. The GFAP positive cells in the 22.5 minute group have a morphology typical of hypertrophic or reactive astrocytes (lower left), where the stain is GFAP immunoreactivity. This reaction is typical of a "subtle" white matter injury.

Thus, we believe that loss or reduction of activity in the upper portion or spectral edge of the EEG frequency domain particularly in the imature brain is predictive of neural dysfunction, while EEG intensity is not. Furthermore, absence of higher spectral edge frequency is predictive of the type of neural injury that has occurred.

Artifacts

The intensive data reduction which converts the signals continuously obtained from each channel into a single number stored once per minute, coupled with the presumption that persons using the BRM are not required to be specifically conversant with EEG technology and related problems, plus the risk that any automatic and largely invisible process for error correction may instead remove biological changes, means that the use of artifact rejection methods must be applied carefully yet effectively.

By "artifacts" we mean false signals that can be confused, by a spectral edge sensing process, with the input signals derived from stable activity of the underlying brain. A hospital ward is by no means an ideal location for EEG recording, especially over a long period and where the patient requires continual care and frequent handling. The signal is of very low amplitude and may fall further in certain disease processes.

Externally-generated artifacts arise from electrical interference and include mains leakage, imbalanced three-phase loads and harmonic currents of the mains frequency induced in any conductors as a result of coupling by magnetic fluxes or earth loops. Switching and lightning-caused transients may enter an EEG input. Diathermy/electrocautery machines, cellular telephones, computers, and other sources of high-frequency interference may interact with EEG recordings.

Subject-associated artifacts include those caused externally, such as by providing care to the subject and inevitably generating movement artifacts, as well as intrinsic (myoelectric) signals derived from the subject's heart and from muscle movements, spasms and seizures, from neural seizures, and from respiratory movements. Further, the brains of some subjects, especially neonates, exhibit periods of electrical silence; and the BRM should simply reject the electrical noise (expressed as a spectral edge) which remains apparent at such times. Older babies exhibit sleep-state cycling of the EEG which would affect the spectral edge measurement.

Artifact Rejection

Figure 11:
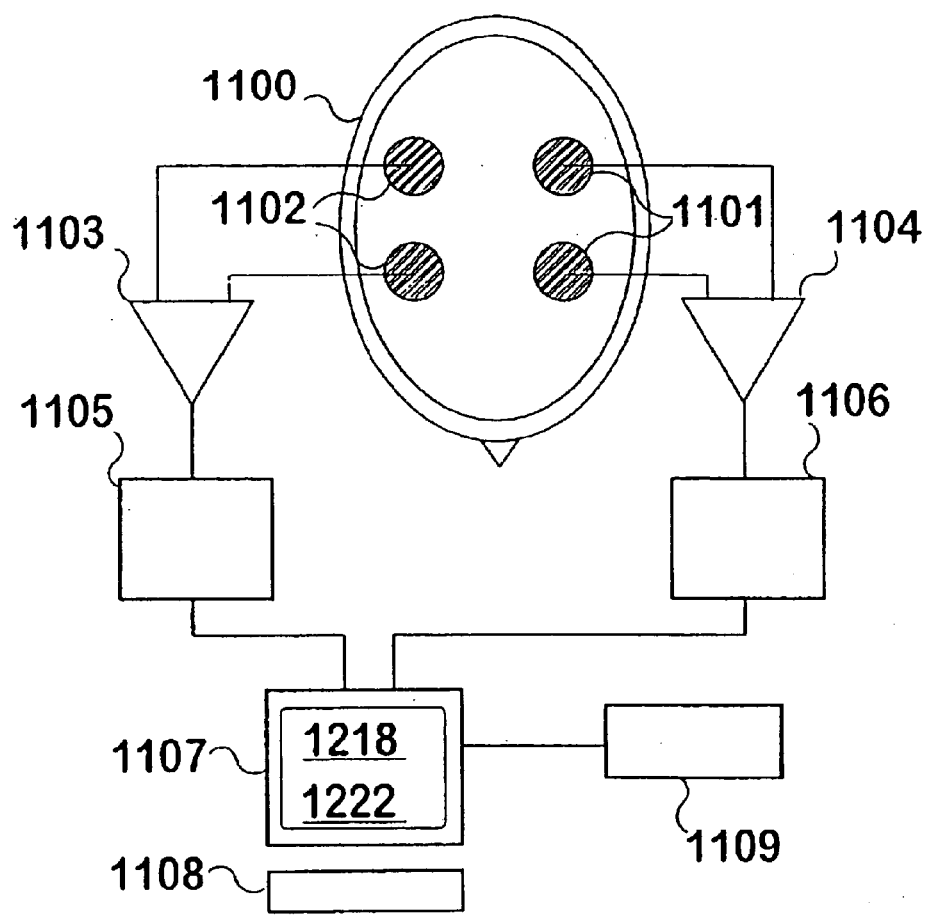
FIG. 11 is a schematic diagram of a brain rescue monitor (RM of this invention.

The brain rescue monitor (BRM) is a device for the storage and display of derivatives, such as selected aspects of the frequency distribution, of EEG signals during and after continuous collection over an extended period of perhaps from an hour up to several days and even a week. Current versions store and display trends occurring in the spectral edge (as herein defined) and also trends in EEG intensity. Those derivatives are correlated with underlying white-matter pathology. EEG signals are collected from cranially applied skin electrodes (pairs 1101, 1102) which may be applied over the site of the suspected lesion, or as part of a standard EEG layout. Preferably both sides of the head are monitored. The entire software processor is shown in FIG. 11 as 1105, and 1106, for the preferred two channels. Software is at present written in LabVIEW™ but may be rewritten in, or automatically converted to, another language such as C++.

The BRM may be provided in two parts: a headstage and a processor. The headstage includes suitable pre-amplifiers, digitizers, and optionally other functions such as electrode and cranial impedance measurement, mechanical movement signal, and photodiode signal processing. The headstage is joined by low-level analog input cabling to the patient, and by a digital carrier (wire, optical fiber, or radio (e.g. using the "Bluetooth" standard) to what may be a standard personal computer (more preferably a laptop, but with the usual controls concealed from general access) running the specific hardware. Versions of the BRM as sold may also include: (a) software (the algorithms), for inclusion in other manufacturers' products, (b) electronic modules, for inclusion in other manufacturers' products, and (c) disposable electronic modules. Both (b) and (c) would include an embedded processor and supporting devices.

Standard EEG preamplifier practice is followed for the BRM headstage, (except that the simplified array of electrodes; see FIG. 11) uses just two channels of differential amplification (amplifiers 1103, 1104). Current injection is a useful addition, for impedance monitoring (see later). The EEG from each pair of scalp electrodes is processed by an amplifier with a gain of 5000, and a pass-band of 1 Hz to 50 Hz (single pole high-pass filter at 1 Hz (−3 dB), 4-pole low-pass Butterworth filter at 50 Hz (−3 dB)). The signal is then digitized at 256 samples per second. Apart from the initial frequency limiting, all signal-processing techniques used in this example employ digital rather than analog processing. The A-D converter makes 12-bit numbers, the program uses double-precision real number variables, and the stored results are single-precision real numbers (4 bytes in size).

The EEG preamplifier is monitored for saturation caused by a DC drift at the input usually as a result of a DC offset caused by an electrode becoming even partly detached from the patient. The amplified DC signal may cause saturation (clipping) of the preamplifier. The spectral edge derived from any epoch of the EEG where the input pre-amplifier is saturated is rejected.

FIG. 11 also shows a graphic display device (CRT) 1107, and an optional printer 1109. The block 1108 represents a pointing device (such as a mouse) used to control the BRM by means of on-screen buttons. In practice, 1105, 1106, 1107, 1108 and storage means 1214 may be functional parts of a personal computer, such as a laptop or similar. 1105 and 1106 may be within a headstage.

Figure 12:
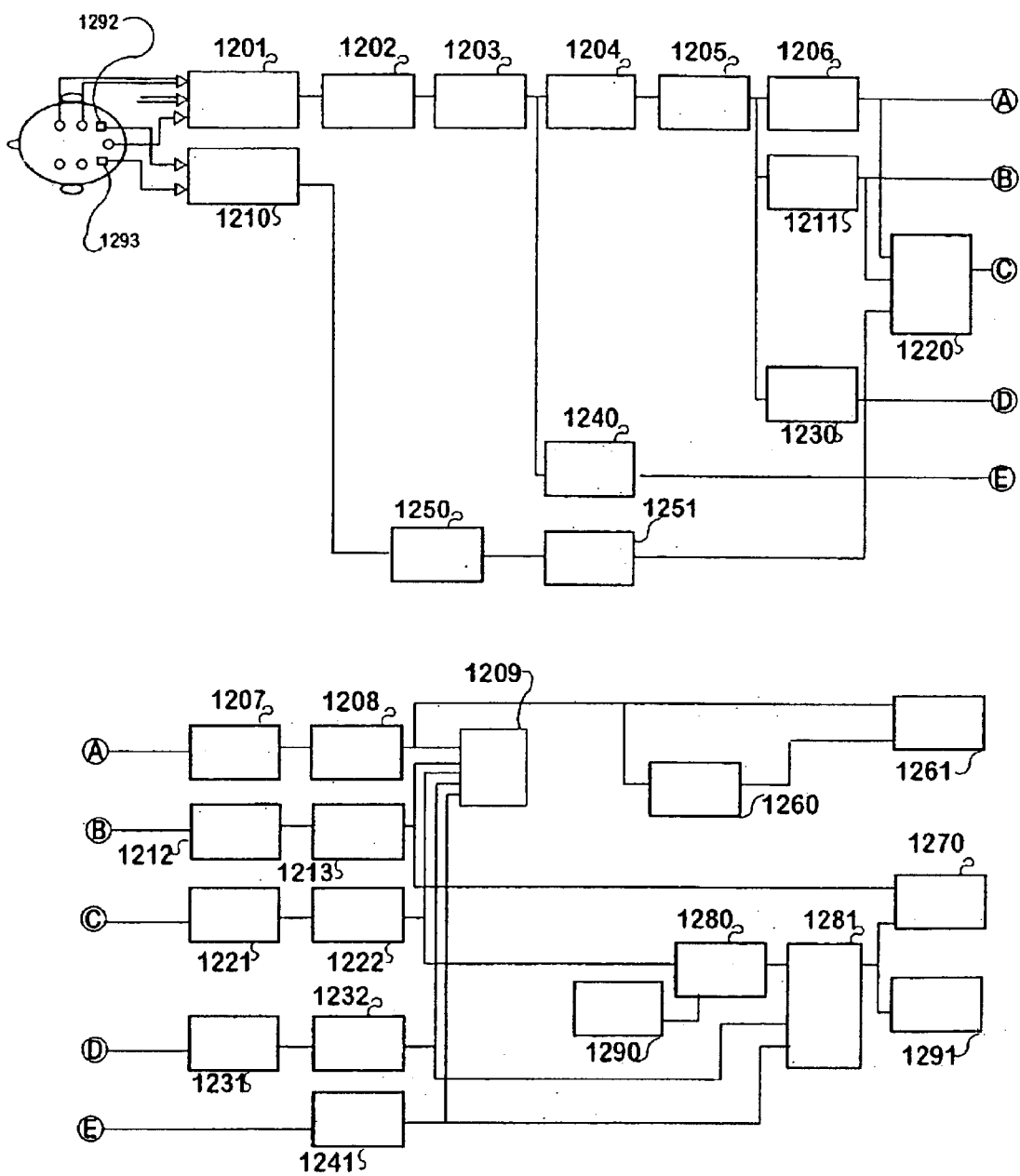
FIG. 12 is a block diagram of the signal processing elements of a BRM.

FIG. 12 shows the block diagram of a preferred form of the BRM. (The drawing is presented in two sections, joined by a row of connectors at (A)–(E); and for simplicity depicts a single channel although two are actually used). A head is shown diagrammatically at top left, with two pairs of active electrodes applied (as described previously) and also one pair of artifact sensors (1292, 1293), for details of which see FIG. 15 and related text. The head stage includes 1201, an EEG amplifier and current injection module. 1202 is an A–D converter, preferably 12 bits at 512 Hz. After the digitization stage, all blocks are preferably software modules, such as may be assembled using functions provided by LabVIEW™. The data stream passes through a median filter 1203, to decimate the signal to 256 Hz and through a detrend module 1204 to a fast Fourier transform (FFT) module 1205. A Fourier transform (FFT) is calculated on consecutive 4 second (1024 point) epochs of the EEG signal. The resulting power spectrum, used for spectral edge (2–20 Hz) (1211) and for extracting (1230) the electrode impedance (see elsewhere) gives measurements of EEG intensity at frequency intervals of 0.25 Hz. Two display measurements are calculated from the power spectrum; spectral edge frequency (in 1211) and total EEG intensity (in 1206). In order to calculate a 90% spectral edge, a routine provided within LabVIEW™ operates by constructing a graph of the spectrum over the selected band of frequencies, then makes a cumulative graph, then divides the total intensity by itself so that the maximum point=1, and finally returns the point on the curve that equals 0.9. Note that the definitions of these measurements as used herein are not necessarily limited to the numerical ranges (such as 2–20 Hz or 90%) as given. For example older subjects, even adults, may be better served by other ranges. We have included age of the subject as a parameter for filter characteristic selection.

The EEG intensity output (A) from the FFT module is passed through a first 5-point median filter (1207) (with 4-second epochs, meaning that this filter has a 20 seconds time constant) then through a 1 minute averaging filter 1208 and may be stored (in 1209) in the form of one number every 60 sec and/or viewed as a part of a trace in a graph 1261 on the display device 1107. See FIGS. 19 and 20 for screen images. The one minute averages may then be displayed in a light gray color as a background plot on the graph (see FIGS. 19 and 20). A smoothed version of the background plot is created by use of a smoothing filter 1260, and shown as a foreground plot in a darker color overlaid on the same graph. This foreground plot gives an indication of the long term trend.

Figure 14:
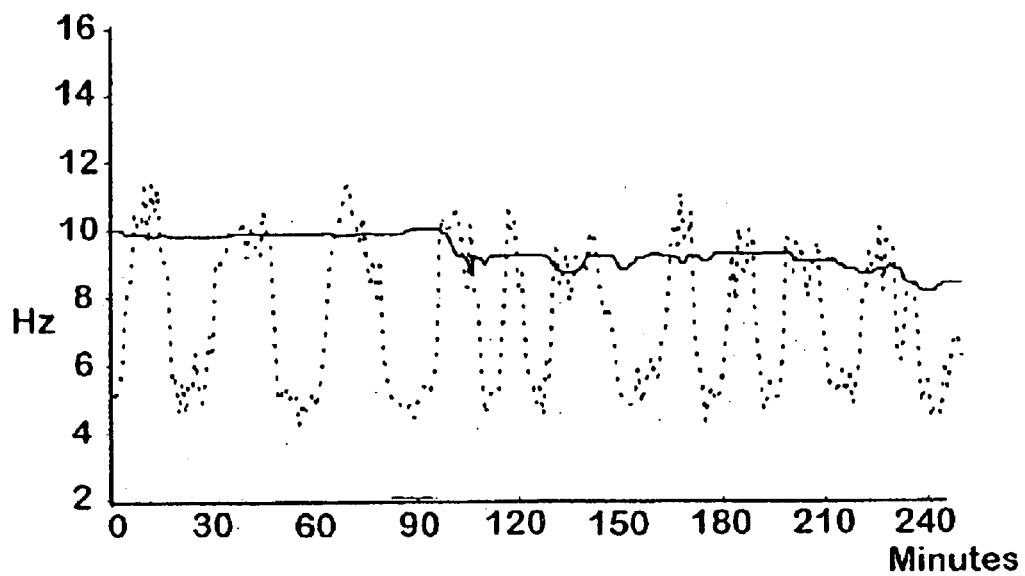
FIG. 14 is a graph showing the effect of the 75th percentile filter on sleep cycles in >34 week babies.

The smoothing filter used is a non-linear filter with a filter length of one hour, which could be switched between a median filter (which tracks the 50th percentile), and a similar filter which tracks the 75th percentile. The 75th percentile filter is intended more for older babies where sleep-state cycling of the EEG would affect the spectral edge measurement. (Subject age is a variable to be entered when the BRM is being set up; and the software selects an appropriate percentile accordingly). During periods of slow-wave sleep the spectral edge frequency would be misleadingly low, and the 75th percentile filter would tend to track the periods of non slow-wave sleep. FIG. 14 shows operation of this sort of filter. Data including sleep patterns from an older neonate (raw as dotted curves, including dramatic falls of spectral edge) is smoothed by a non-linear filter to create the solid line. The time constant of the filter is selected so that clinically significant long-term drops of spectral edge are displayed as such, in older babies, while short-term drops are also displayed for younger babies.

The spectral edge data flow starting from the FFT module (1205) is split into two paths. The first spectral edge path 1211 proceeds through a second 5 point (20 sec) median filter 1212 then a 1 minute averaging filter 1213 as one measurement of spectral edge per minute, again capable of being stored (in 1209) and/or viewed as visible plotted information 1270.

Figure 13:
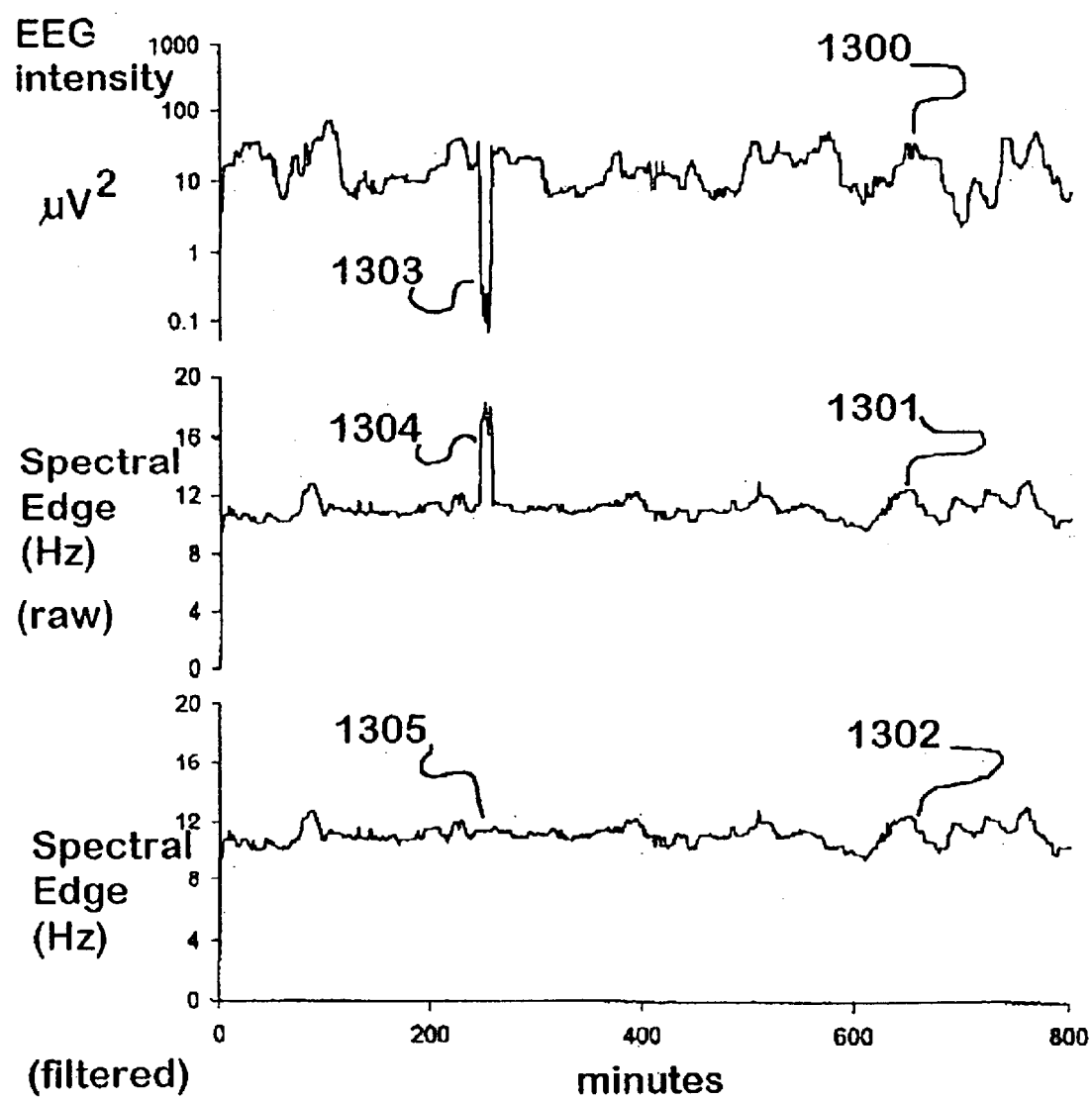
FIG. 13 is a graph showing the effect of an amplitude threshold filter on the spectral edge display.
Figure 15:
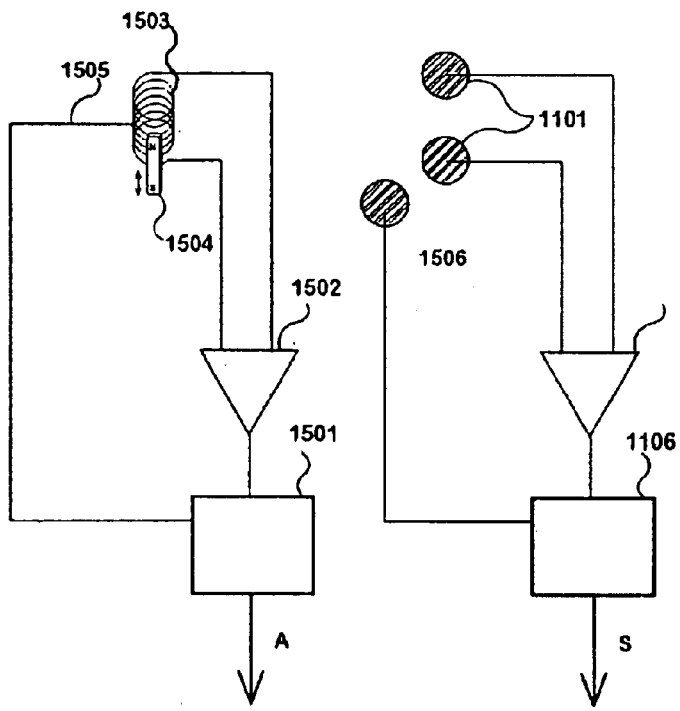
FIG. 15 is a schematic showing the use of phantom or simulated electrodes for movement detection.

The second spectral edge path first enters a spectral edge validation gate 1220, capable of cutting inputs in the event of (a) if, and only if, the amplitude lies between a lower and an upper threshold, (b) in the absence of movement artifact information, (which has been picked up from a motion detector such as that of FIG. 15, amplified in 1210, digitized in 1250, and processed in 1251), and (c) if seizure detector 1240, which samples analog inputs, is quiescent as indicated by a zero or low count in seizure counter 1241. The threshold filter is particularly useful for avoiding spurious displays of the spectral edge of electronic noise when the brain under study enters an inactive phase, and the incoming intensity drops so low that electronic noise predominates, and for rejecting artifacts which usually exceed the upper threshold. We prefer 0.5 $\mu V$ as a low threshold and 500 $\mu V$ as an upper threshold, but these values may be varied according to experience under different circumstances. Again, the signal passes through a median filter (1221) having a 20 seconds time constant, then a 1 minute averaging filter 1222, hence also "formatted" as one number every minute for storage (1209) and/or viewing (1270). FIG. 13 shows how the threshold filter deletes disturbances from the spectral edge channel.

The modules that extract electrode impedance information from the signals (which is created by the injection of a known small current (e.g. 1 nA) at spot frequencies above the spectrum of relevance to spectral edge) are 1230, a selective detector which may be a synchronous detector, followed by median filter 1231 and averaging filter 1232 as for the other channels.

Spectral edge validation, either blanking out, or interpolating through, periods interrupted by artifacts such as seizures, is performed in module 1281. Its inputs comprise spectral edge information passed through sleep state filter 1280, and controlled by gestational age input 1290, also seizure events and also electrode impedance.

At this point, "storage" at block 1209 comprises the recording of a set of three 32-bit numbers (and sign) from minmally channels A, B, and C (intensity, spectral edge, and validated spectral edge) once a minute or more preferably adding electrode impedance and seizure counts as two further channels. Channels A, B, and C are derived from one of the two pairs of electrodes. Any one or more convenient write/read storage means may be used, such as flash RAM, hard disk, or the like; even a remote storage device such as within a computer network. The system is economical of storage; 64 K bytes is filled in about 45 hours or almost 2 days in the 3-channel mode. It is always preferable to reduce the quantity of raw data as far as possible and here the volume compression ratio after A–D conversion is about 1000:1. Raw EEG traces are not inspected during monitoring by the BRM.

Artifact Management

To ensure that only highly reliable data is displayed, several sources of artifact are monitored and the spectral edge of any four-second epoch of EEG contaminated by artifact is rejected from the one minute average. If all 15 epochs in any one minute period are rejected due to artifact contamination, then this portion of the graph is blanked out. One version of the invention which carries out that function was described with reference to FIG. 12.

Monitoring steps include some or all of the following:

Preferred EEG electrode strips have embedded or attached movement sensors to detect. movement of the baby which may contaminate the EEG signal. This movement could come from high-frequency ventilators which vibrate the baby at about 10–15 Hz, or from gross movements of the baby or the electrode cable such as when handled by nursing staff. Excess movement artifact from high frequency ventilators would tend to falsely raise the spectral edge frequency. Other movements of the baby or electrode cable occur at a much lower frequency and would tend to falsely lower the spectral edge frequency. If the movement is considered excessive, then the spectral edge from the affected epoch is rejected.

A type of movement sensor (assumed to be in use for the description of FIG. 12) is shown in FIG. 15. The purpose of this device is to create an electric signal whenever the baby (and in particular its head) moves, whenever the incubator moves, or whenever the cable carrying the low-level signals is tapped, causing "microphonics". Any such voltage will be amplified in the headstage and supplied as signal "A" (for artifact) to the BRM. This signal may be used in several ways, but preferably by causing the EEG input to be gated for the duration of the interference so that the spectral edge measurements are not corrupted. For this to occur, the signals from the movement sensor is preferably amplified and digitized as for the signals from the active electrodes, and gating (optionally following signal recognition) is then carried out in software. The digitizing may be carried out at a lower resolution than that used for the EEG signals. FIG. 15 shows an example movement sensor; an open, wound coil 1503 within which a magnetized mass 1504 is suspended in a manner which allows the mass to move relative to the coil during any form of impact. This coil is grounded 1505 at a center-tap for balance, but optionally may better serve as an artifact pickup if not. As a coil, it can also detect electromagnetic interference. Several such coils arranged in different axes; their resulting currents combined in a resistor matrix, may be more effective. An alternative is a silicon fabricated sensor of the type developed as an accelerometer for setting off an air bag in a vehicle, but the supply of DC power to the accelerometer chip may comprise a problem.

The total EEG intensity is monitored to ensure that it falls in the valid range. If the total EEG intensity is too low (<0.5 $\mu V^2$ for example), this could indicate a pre-term baby showing a trace-alternant pattern of EEG where the EEG goes flat for periods, or a problem with the EEG electrodes (electrodes too close together and shorting out for example), or EEG signal affected by anesthetic. The spectral edge frequency measured from a low-intensity EEG signal would be unreliable.

The BRM may include means (see 1290 in FIG. 12) to adapt criteria for filtering and for assessing measured parameters according to gestational age, which can be entered at the start of a recording session. For example, babies over 34 weeks may exhibit periods of "slow wave sleep" as a normal event. One kind of filter to avoid rating such an event as abnormal comprises a median filter of extended time coverage, and its performance is shown in FIG. 14. For another example, we observe a strong correlation between spectral edge frequency (not for amplitude or intensity) and corrected gestational age (r=0.64, p=0.001) after 32 weeks, but not before (r=0.09, not significant) (see Buckland et al., op. cit.). Optionally the BRM can be programmed to "demand" a sufficiently long uninterrupted period of data collection (such as at least 2 hours) for babies over 34 weeks to ensure that a slow wave sleep period does not corrupt the recording.

If the total EEG intensity is too high (>500 $\mu V^2$ for example), this could indicate excessive movement artifact, or contamination by seizure activity, either of which would lead to a false measure of spectral edge frequency. The description of FIG. 12 assumes that we handle large amplitude signals and seizures separately, which may not be necessary.

Given that a high correlation in all measures between both hemispheres is observed (Buckland et al., op. cit.) for all measures (r>0.8), the BRM should be programmed to regard clear differences in sensed parameters between hemispheres as more likely to indicate an artifact (a fault) than a subject effect, and in any case, call attention to the problem. There is a difference in outcomes for babies where only one hemisphere is affected; the other may "take over" functions, as opposed to bilateral WMI where there is nothing to take over.

The spectral edge of any epoch of EEG with an intensity outside the valid range is rejected. FIG. 13 shows the effect of the amplitude bandpass filter. The top curve 1300 shows EEG intensity against time; where the time scale extends over about 12 hours, and the intensity is shown logarithmically. Note the period 1303 where the signal temporarily goes below 0.5 $\mu V$. The middle curve 1301 shows a raw, uncorrected spectral edge curve. At the time when the signal amplitude was so low that it was lost in noise, 1304 shows a sudden rise in spectral edge (probably where white noise was treated as signal) which might interfere with machine or human analysis. The bottom curve 1302 shows the post-filter spectral edge curve where the aberrant peak 1304 has been removed at the position 1305.

The raw EEG signal is monitored for too large an amplitude, or clipping of the signal. This could be due, for example, to large voltage spikes on the input amplifiers from cardiac defibrillators, or electrosurgery units. The EEG pre-amplifier is monitored for saturation. If one of the electrodes becomes detached from the patient this can cause saturation of the pre-amplifier (shown first as clipping, and eventually silence) when the output voltage of the pre-amplifier drifts up to the positive or down to the negative supply voltage. The spectral edge of any epoch of the EEG where the input pre-amplifier is saturated, too large, or is clipped is rejected.

The electrode impedance is preferably monitored continuously by the brain rescue monitor, on both sides of the head of the patient. This is conveniently carried out by injecting a 1 nA sinusoidal current at 35 Hz through one electrode pair and 42 Hz through the electrode pair on the other side). The electrode impedances are measured by measuring the size of the peaks in the EEG intensity spectrum at 35 and 42 Hz (module 1240 with 1241 in FIG. 12). If the electrode impedance is too high this indicates a poor electrical contact with the patient, leading to increased movement artifact, increased noise levels and increased susceptibility to electromagnetic interference. If the electrode impedance is too low, the electrodes may be touching or are bridged by too much electrode gel on the skin causing shorting of the electrodes. The spectral edge of any epoch of the EEG where the electrode impedance is too high or too low is rejected.

The EEG is continuously monitored for seizure and spike activity. Seizures are large amplitude, low frequency events which tend to falsely lower the spectral edge frequency. The spectral edge of any epoch affected by seizures is rejected.

Additionally, the EEG is monitored for electrical interference. The spectral edge of any signal affected by electrical interference is rejected.

The electrode strips may have an identification code built into them, generally in the form of a digitally readable chip such as a memory module or one of the uniquely encoded "Dallas" identifying chips. If identification chips are present, the EEG headstage periodically interrogates the electrode strip to ensure that the correct type of electrode is being used. If the wrong type of electrode strip is being used, or the electrode strip becomes detached from the input lead, then the spectral edge from any affected epoch is rejected. If the same electrode strip has been in use for more than a set number of days, the BRM indicates that it is time to change it. Alternatively, the resistors used in the phantom electrode of approach 2 (FIG. 15) may be measured by the BRM, using the same impedance monitoring procedure as is used for the skin impedance test. The impedance between a first and a second active input (dependent on a selection of resistors) may be chosen to indicate one of a variety of types of electrode.

Figure 19:
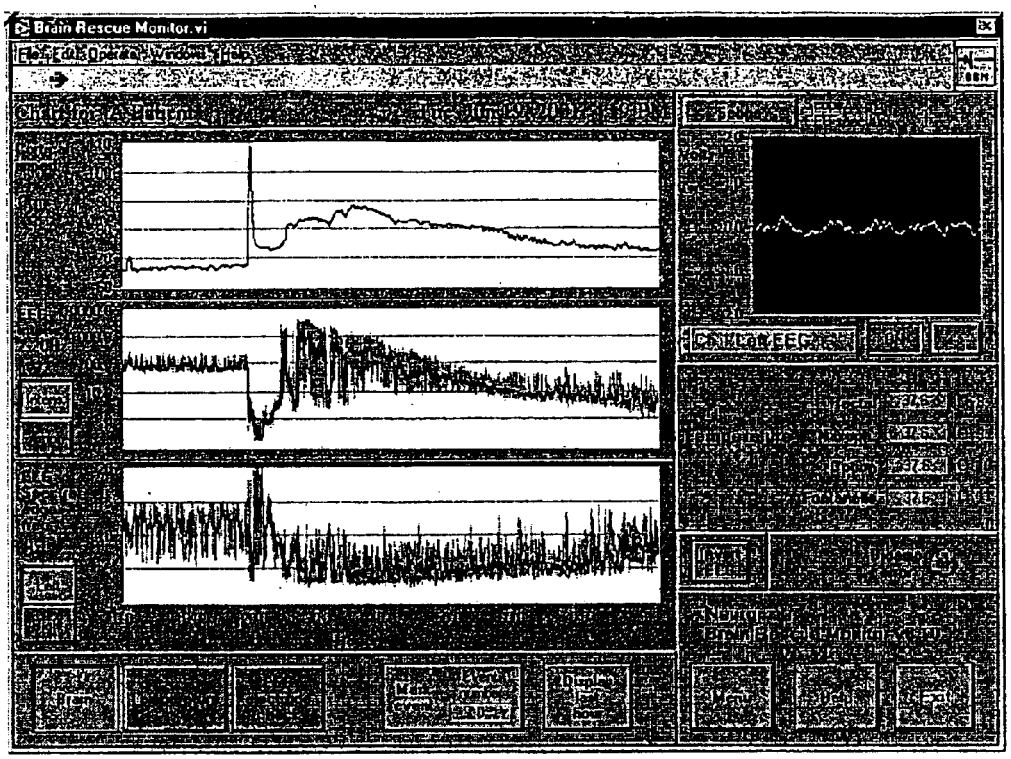
FIG. 19 is a screen image from a BRM of this invention, showing the monitoring of a sheep over 80 hrs, including cortical impedance, EEG intensity, and spectral edge frequency.

Skin temperature is recorded from at least some of our electrode sets and may be displayed (see FIG. 19). It may be recorded and if associated with any particular kind of artifact it can enter into the filtering process. Use of cooling caps is likely to influence the EEG characteristics.

Given an instrument in which internal signal processing is capable of detecting artifacts within an incoming signal that, being a very low amplitude bioelecttical signal, is inherently liable to adverse effects, it is possible to provide a number of guides to a user which indicate what is wrong with an incoming signal, and how to correct the defects. Particularly for a case where the actual EEG signals are processed so much before display, an instrument which issues a "reject" verdict without any reason would be very frustrating to use and maintain in a reliable state.

Figure 16:
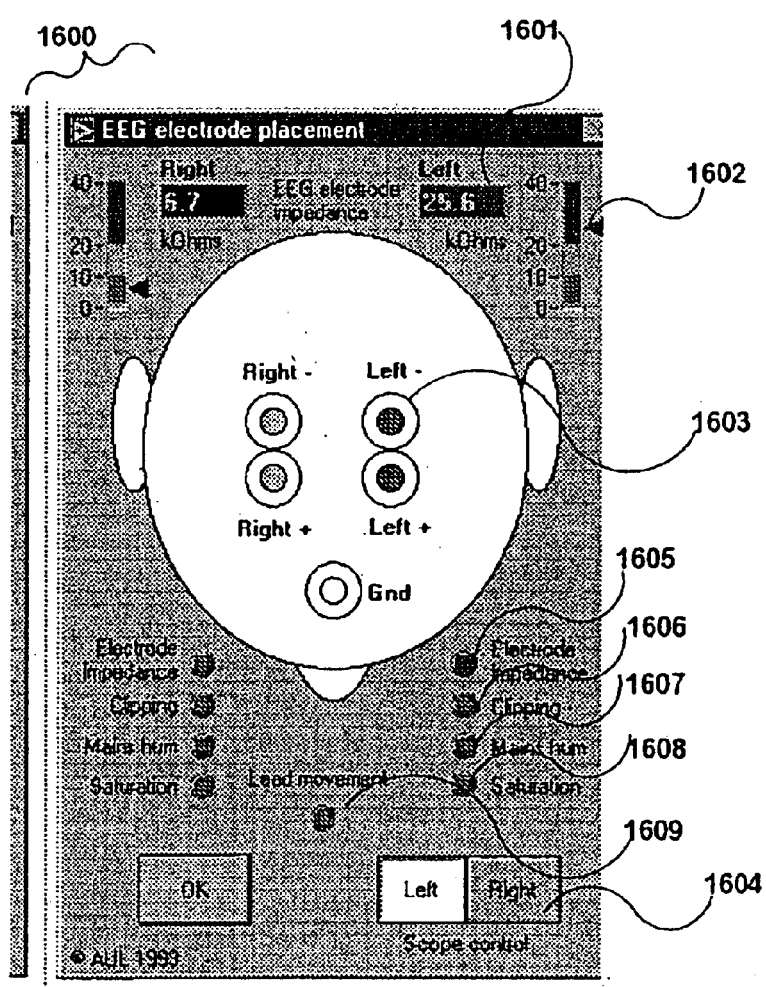
FIG. 16 is an example of a display providing feedback for a person setting up the electrodes and recording conditions, based on detection of aberrant conditions by particular filter sets within the BRM.

A simple user diagnostic display 1600 is shown in FIG. 16. This is intended to bridge the gap between normal nursing skills and specialist EEG technician skills. The display is initially presented on the BRM graphic display during lead placement, and includes a head map to show approximate electrode positions, and also includes the results of machine assessments of signal quality made during setting up and running. Electrode impedance on each side is indicated as a number (1601) and as a good/tolerable-bad bar graph (1602). A set of lights for each side (left= 1605–1609) shows specific faults/artifacts. by becoming lit, so that the user can go to a context-sensitive help file (also available through the graphical display, which is preferably touch-sensitive) and be told what to do. Preferably the user will be guided towards specific steps to reduce the kind of artifact being detected. The left/right button 1604 selects which of the two hemisphere inputs is to be shown on the virtual oscilloscope elsewhere on the display. A virtual indicator lamp (1609) is lit when the filters consider that the incoming signal includes movement artifacts (cf. FIG. 15). Optionally, a rating of signal quality can also be displayed to the user. This may be expressed as a number between 0 and 100 which indicates the percentage of valid epochs in any one minute period.

Electrode placement may be developed further, by including a facility for accepting head size and shape measurements into the BRM (as coordinated by a display indicating where the first or next measurement is to be taken) during first placement of electrodes, and displaying an image of a baby's head of corresponding dimensions and shape in a 3D form, so that the electrode placement conforms as closely as is feasible to the intended standard placement (currently, according to the "10–20" system).

Figure 20:
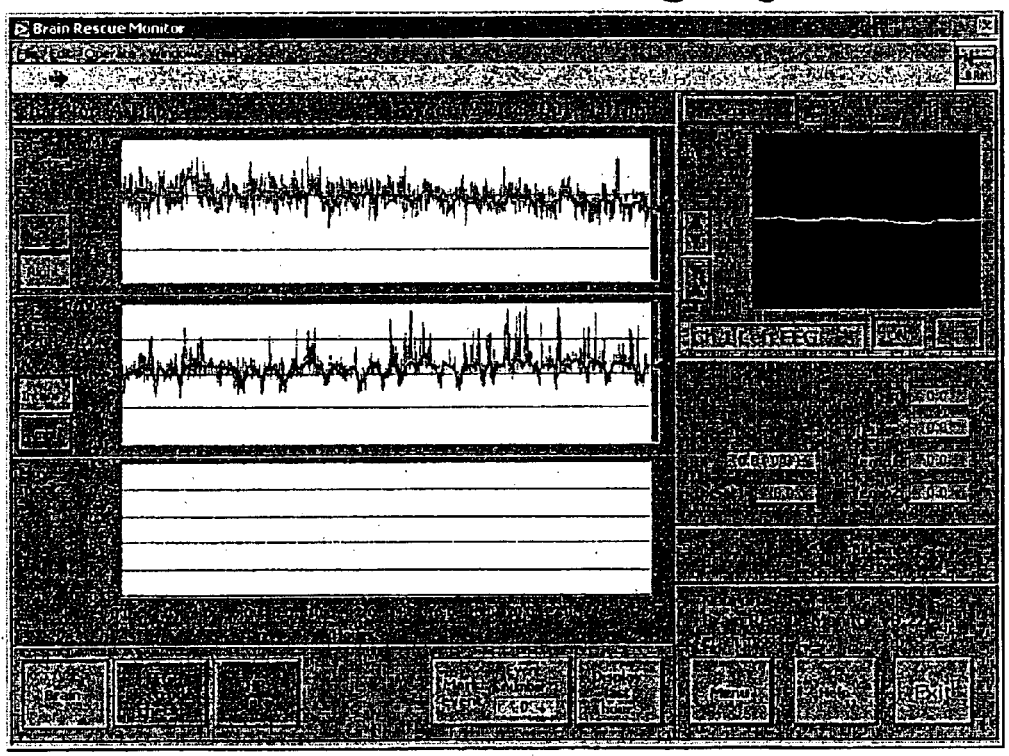
FIG. 20 is a screen image from a BRM of this invention, showing the monitoring of a pre-term infant with white matter damage over 26 hours, including spectral edge frequency and EEG intensity.

FIGS. 19 and 20 show typical screen layouts, with illustrative data sets, for the BRM. Since it is a virtual instrument, simulated by a computer, we have freedom to vary its layout. FIG. 19 shows an ovine carotid ligation experiment run over 3½ days, and includes a cortical impedance trace (top trace), EEG intensity (middle trace) and spectral edge (bottom trace). FIG. 20 is from a baby with WMI. The left trace showed an even lower spectral edge of around 8 Hz. (The movement sensor display was inoperative in this run)

Diagnostic Uses

This table (from Inder et al) shows in statistical form a dependence of upper quartile spectral edge on the extent of white matter injury, as displayed by magnetic resonance imaging as assessed by a qualified pediatric neuroradiologist in a blinded situation. The number "n" refers to hemispheres, not infants.

Values shown are median level the 25th and 75th percentile box, the 10th and 90th percentiles as error bars, and individual outliers.

One could express these results in terms of clinically useful guidelines as follows: if the spectral edge value is below 6 Hz there is a likelihood of cystic white matter injury (WMI); if the spectral edge value is between 6 and 8 Hz there is a likelihood of moderate WMI; if the spectral edge value is between 8 and 10 Hz there is a likelihood of mild WMI; while if the spectral edge is above 10 Hz there is little likelihood of WMI (see FIG. 18) Less specifically, guidelines may be as follows: if the spectral edge value is below 8 Hz there is a high likelihood of injury; if the spectral edge value is between 8 and 10 Hz the infant requires further monitoring; while if the spectral edge is above 10 Hz there is a high likelihood that no injury exists. It must be remembered that these guidelines ate provided here purely as initial suggestions, before any significant amount of clinical research, including long-term follow-ups has taken place. Directed clinical intervention under a "rescue" objective is also likely to alter outcomes.

Employing the BRM

The BRM is on trial in several neonatal intensive care units where the present standard for quantifying brain damage is MRI, in preference to ultrasound imaging. The significance of variations in the spectral edge over time is not understood for all cases. At the time of filing, data is lacking in particular in relation to eventual outcomes. Nevertheless we can suggest several ways to use the BRM in a neonatal intensive care unit.

In a first option, all infants are monitored continuously, with a separate BRM connected to each one. In this mode any unexpected change is noticed in time for neuronal rescue therapy to be effective whereas under option 2 it may not be. Dips in the spectral edge line may occur over short periods. They may be evidence of injuries though dips or

|  | Cystic WMI (n = 4) | Moderate WMI (n = 16) | Mild WMI (n = 36) | Normal (n = 52) | p-value (Kruskal-Wallis) |
|---|---|---|---|---|---|
| Upper quartile spectral edge (Hz) | 6.0 (5.6–6.5) | 7.9 (4.9–11.4) | 9.9 (5.7–11.2) | 11.2 (8.0–14.9) | <0.001 |

Severe WMI is considered to include cystic white matter injury and ventriculomegaly, consistent with diffuse loss of white matter volume; moderate WMI is considered to be as above but without cysts, mild WMI is considered to include focal white matter signal abnormality but neither cysts not definite ventriculomegaly.

Figure 17:
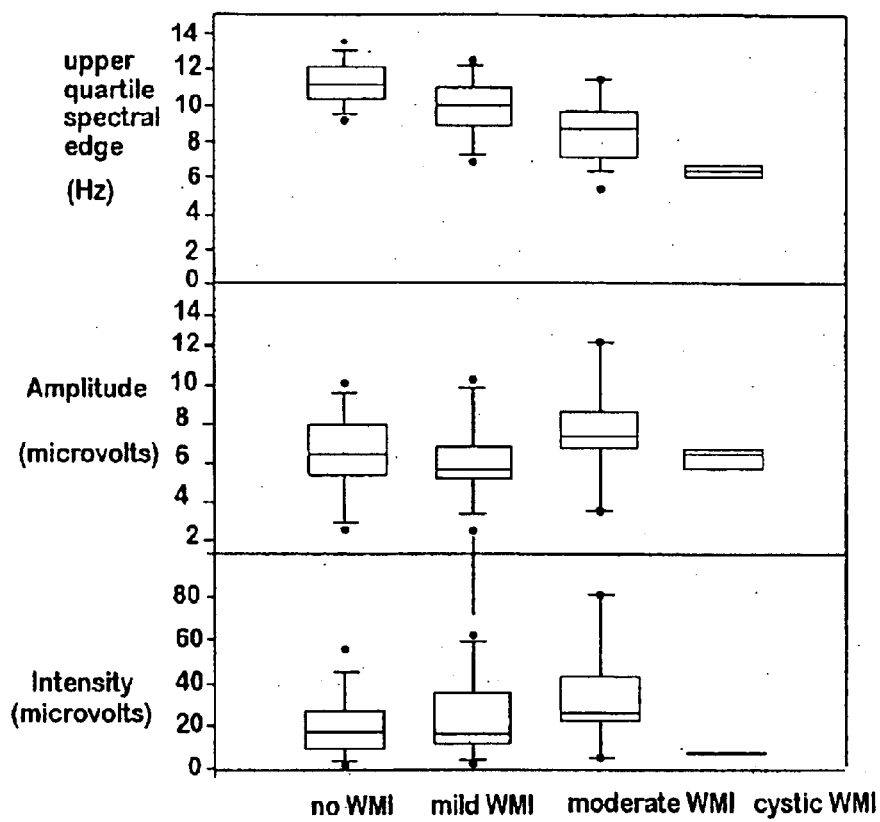
FIG. 17 is a graph (from Inder et al.) comparing three EEG derivatives as potential indicators of white-matter injury (WMI).

FIG. 17 (also from Inder et al.) compares upper quartile spectral edge, EEG intensity, and amplitude, in order to amplify the individual contributions to the above table. The median level, the 25th and 75th percentiles (box boundaries), the 10th/90th percentiles (error bars) and a scattered outlier are shown. Controlling the analysis of the relationship of spectral edge with white matter injury for gestational age as a covariate did not affect the significance of the relationship (ANOVA F=31.125, 3 degrees of freedom, p<0.001).

Figure 18:
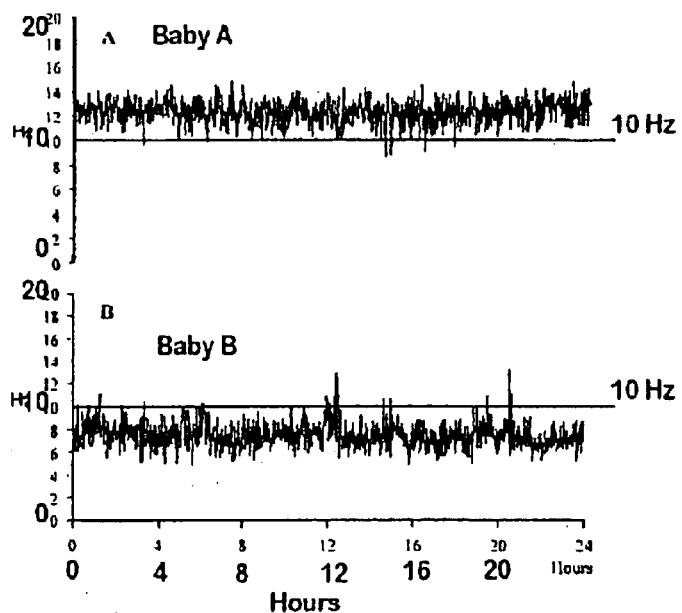
FIG. 18 is a graph (from Inder et al) comparing spectral edge readings once per minute over 24 hours from baby A (normal) and baby B (with WMI) as an indicator of WMI.

FIG. 18 graphically shows 24-hour BRM output from two representative babies, as 1-minute averaged spectral edge curves. Baby A (top curve) is normal, while Baby B is not, and the spectral edge curve is consistently lower. Note that the 10 Hz line has been produced across each curve. In FIG. 17, various states of white matter injury (WMI) are shown.

low readings can sometimes be related to infection or metabolic problems. It is very useful to be able to scan over earlier recordings from the infant, if an unclear situation arises.

In a second option, all infants are screened for risk, on entry and preferably as a routine check every few days, such as days 1, 2, 3, 4, 7, 14, and 28 days after birth. Deterioration is most likely to occur particularly over the first 2 to 3 weeks of life if it is not already present at birth. Any infant whose spectral edge indicates likely injury is moved to approach no. 3. A period of from 15 min to 3 hours, such as 90 minutes, of data collection is suggested for each screening, particularly of preterm infants; and a longer time, such as 2 hours, may be appropriate for older infants. Trend monitoring typically requires a shorter time, such as 15 to 30 minutes, for example 20 minutes. Buckland's paper employed 4 collections of data from both hermispheres each collected over 2 hours. The first was collected as early as possible after birth, then at days 14, 21, and 28. Indications from that study are that the critical, most vulnerable, period during the first two weeks, when significant changes were noticed, justifies continuous use in an intensive care neonatal unit. In contrast there was high correlation from day 14 to day 28 (r>0.4, p<0.01).

In a third option, continuous monitoring, or at least monitoring at regular intervals, is performed of at-risk infants for management and treatment, and consideration of likely outcome.

In a fourth option, all infants are screened on exit with the intention of checking their neural status some time later. This is relevant to gaining further understanding of relationships between signs and eventual outcome. Medicolegal aspects of neonatal care tend towards more and more assessments and recordings particular in relation to neural status.

In another option, during labor, any infant considered to be at risk may be monitored. Intrapartum monitoring is relevant in relation to the risk of development of cerebral palsy and possible remedial action. Screw electrodes are acceptable in this situation. There is a large probability of corruption of EEG signals by extraneous artifacts, which are dealt with largely on the amplitude discrimination criteria. Our fetal sheep experiments comprise a model of hypoperfusion in labor. See FIGS. 4a, 5a and 7 relating to a 15 minute cerebral hypoperfusion injury, causing an acute rise in cortical impedance (a measure of cytotoxic edema), and a loss of spectral edge frequency in the EEG signal. These features rapidly resolved after the hypoperfusion injury.

Variations

Given a module the output of which is capable of acting as a gate, it is advantageous to insert a delay of perhaps one block's worth (typically 2 or 4 seconds) in the signal to be gated, in order that action arising from the fault condition is applied "in advance" to the signal to be gated, so that no signal including the unwanted impulse is transferred either for analysis or to a display.

More than two channels may be processed at one time. For example a whole array of many active pairs of electrodes could be put on a cranium and supervised. This may more specifically locate a focal area of white matter injury. An algorithm can report the anatomical site as referred to the cranium where the lowest spectral edge frequency is being detected, so approximating an imaging function. This extra data also improves the reliability of a forecast of an eventual outcome.

Our use of a fast Fourier transform (FFT) process for conversion into the frequency domain is but one of several possible processes. The FFT can have a particular disadvantage of minimizing occasional spikes because it is inherently a time-averaging process and in our example we prefer to use 4 second duration windows.

Acceptable options which enhance the effectiveness of the invention by preserving possible brief impulses include windowed Fourier transforms (where the ends of each window are scaled towards zero), intensity spectrum analysis, and wavelet-based frequency analysis, (or other related scale-varying basis functions), such as the discrete wavelet transform (DWT). A DWT has variable-length windows, such as long duration windows for the lower range of frequencies (2-10 Hz) and short duration windows for the higher-range (10–25 Hz or more). More than two bands may be analyzed. In order to recover spectral edge information, these signals may be recombined in a matrix. DWT procedures can minimize noise by setting coefficients that are less than a predetermined threshold to zero, which may make the displays of this BRM instrument cleaner and more amenable to human review. Alternative signal processing filters exist, some of which are available within the LabVIEW™ package.

An individual BRM should not adapt itself during use by in effect changing its specifications because consistent recordings are required for comparisons, and because regulatory approval is based on a definite, specified, instrument. Our use of an age-related "filter switch" is predictable; signal-responsive adaptations are unpredictable.

Many forms of programmable digital computer are available for signal processing purposes. Although the currently preferred form is a high-end xx86 family processor, offering convenient interfacing to networks, storage devices and the like (as well as being compatible with LabVIEW™ software), specialized digital signal processing type microprocessors may be advantageous. The software could be replaced with routines written in another high-level language such as the presently popular $C^{++}$ or JAVA.

Instead of measuring the electrode impedance in software, an optional hardware solution involves use of a synchronous detector, which may give a cleaner measurement. The software method previously described assumes that the signal from the injected current will be much larger than the background EEG activity at 35 and 42 Hz. Note also that we may measure impedances from the phantom or simulated electrodes, which adds more test frequencies, although these may be generated and measured only occasionally.

Commercial Benefits or Advantages

A bedside device (the BRM) able to quantify even small amounts of cerebral white matter injury status of a pre-term baby over a long period is of considerable clinical use and may permit clinical intervention (including cooling caps, body cooling, peptide therapy, and the like) leading to alleviation and/or cure of the injury. This leads to fewer permanently affected infants, children, and adults. Given the present frequency of white matter injury, considerable reductions of personal suffering and of national health industry costs are possible.

The BRM relies on signal processing in order to automatically reduce the overwhelming amount of raw EEG data into useful and easily comprehended trends even over long periods. EEG technical skills, both for positioning the equipment and for reading traces, are not essential. The invention simplifies usage of EEG information for clinical purposes.

Rejection of artifacts (and recognition of fault conditions) is provided for by filters and gates designed to be effective in reducing the chance of spurious results being acted upon as if they were genuine results, yet always retaining important information. Movement sensors and the like are also used as indicators of bad recording conditions.

Finally, it will be understood that the scope of this invention as described and/or illustrated within this specification is not limited to the preferred embodiments described herein. Those skilled in the art will appreciate that various modifications, additions, and substitutions are possible without departing from the scope and spirit of the invention as set forth in the following claims. The disclosures of the documents referred to throughout this application are incorporated into this application by reference.

I claim:

1. An apparatus for processing an electroencephalogram (EEG) signal from a subject to assist in management of possible cerebral white-matter neural injury in the subject, comprising:

(a) apparatus to acquire at least one channel of an EEG signal from the subject over a period of time, and (b) computing apparatus programmed to analyze the frequency distribution of the EEG signal so acquired, from within a range of from 1 Hz to 50 Hz, and to produce condensed output information descriptive and/or predictive of cerebral white-matter neural injury in the subject.

2. The apparatus of claim 1 further comprising apparatus programmed to analyze the frequency distribution by determining a numerical value for the upper spectral edge of the frequency distribution of the intensity of the EEG signals.

3. The apparatus of claim 2 further comprising apparatus to determine the spectral edge for each of a series of time intervals, to store a corresponding series of spectral edge values, and to include the series of spectral edge values on a display, thereby to enable forecasting of an outcome of cerebral white-matter neural injury in the subject.

4. The apparatus of claim 3 further comprising apparatus to determine, within the range of 1 Hz to 35 Hz, the upper spectral edge below which about 95% of the EEG intensity occurs.

5. The apparatus of claim 4 further comprising apparatus to provide a comparison of the determined upper spectral edge with stored EEG spectral edge and associated neurological outcome information from previous cases, thereby to enable forecasting of an outcome of cerebral white-matter neural injury in the subject.

6. The apparatus of claim 5 further comprising apparatus to acquire a plurality of channels of EEG signals, so that spectral edge recordings are made from a plurality of positions on the head of the subject, thereby to improve confidence in forecasting outcome of cerebral white-matter neural injury in the subject.

7. A program embodied on a computer readable medium in combination with the apparatus of claim 5, the program comprising a routine to display comparable portions of both a current record and a previously collected record thereby permitting a comparison of the current record with stored information derived from the EEG and neurological outcome information from previous cases, thereby enabling prediction of an outcome of cerebral white-matter neural injury in the subject.

8. The apparatus of claim 4 further comprising apparatus programmed to eliminate an artifact in output information by action of at least one event-responsive filtering procedure to delete from the output information data likely to be in error.

9. The apparatus of claim 8 where the event-responsive filtering procedure is a signal interruption procedure that rejects the determined upper spectral edge during detection of a condition within the EEG signal selected from abnormally low signal amplitude, abnormally high signal amplitude, a signal indicating a seizure in the subject, a signal indicative of sleep in the subject, and a signal indicative of a presence of electrical interference.

10. The apparatus of claim 8 further comprising a movement sensor and where the event-responsive filtering procedure is a signal interruption procedure that rejects the determined upper spectral edge during detection of movement.

11. The apparatus of claim 8 further comprising an electrode impedance detector and where the event-responsive filtering procedure is a signal interruption procedure that rejects the determined upper spectral edged during detection of an incorrect electrode impedance.

12. The apparatus of claim 8 further comprising an electrode identification detector and where the event-responsive filtering procedure is a signal interruption procedure that rejects the determined upper spectral edge during detection of an inappropriate electrode.

13. The apparatus of claim 8 further comprising an input apparatus through which an operator can input information describing the developmental status of the subject and apparatus programmed to make alterations to filter parameters in accordance with known neurophysiological parameters of subjects of that developmental status.

14. The apparatus of claim 8 further comprising apparatus for issuing an appropriate advisory message to an operator for the operator to cause removal of the artifact.

15. A program embodied on a computer readable medium in combination with the apparatus of claim 8, the program comprising a routine to display an annotated image of a head to indicate a suitable position for the placement of EEG electrodes.

16. A program embodied on a computer readable medium in combination with the apparatus of claim 8, the program comprising at least one routine to accept data representing a digitized EEG signal and filter the data to exclude data likely to be in error, thereby facilitating prediction of the outcome of cerebral white-matter neural injury in the subject.

17. The program embodied on a computer readable medium of claim 16 further comprising at least one routine to receive information and to act on the data in response to the information to minimize the effect of an artifact.

18. The program embodied on a computer readable medium of claim 17 further comprising at least one routine to analyze the incoming data to establish the likely presence of an artifact, and, if the likely presence of an artifact is established, to output an advisory message to an operator to cause the removal of the artifact.

19. The apparatus of claim 3 further comprising apparatus to determine, between 2 Hz and 20 Hz, the upper spectral edge below which about 90% of the EEG intensity occurs.

20. A method for using the apparatus of claim 3 including screening at least one subject from time to time by using the apparatus to define the characteristics of the EEG of the subject to determine whether the subject being screened is at risk of cerebral white-matter neural injury to allow treatment and or forecasts of likely outcomes to be made accordingly.

21. A method for using the apparatus of claim 3 including continuously monitoring at least one subject by using the apparatus to define and follow the characteristics of the EEG of the subject in order to determine the presence and extent of cerebral white-matter neural injury to allow effectiveness of any treatment of the subject to be monitored and/or to allow a forecast of likely outcome to be made.

22. A program embodied on a computer readable medium in combination with the apparatus of claim 2, the program comprising a routine to accept data representing a digitized EEG signal and provide an output representing a numerical value for the upper spectral edge of the frequency distribution of the intensity within the EEG signal.

23. A program embodied on a computer readable medium in combination with the apparatus of claim 1, the program comprising a routine to accept data representing a digitized EEG signal and provide an output representing a numerical value for condensed output information descriptive and/or predictive of cerebral white-matter neural injury in the subject.

24. A method for predicting cerebral white-matter neural injury in a subject comprising acquiring, over a period of time, an EEG signal from the subject, analyzing a frequency distribution of the signal within the range of about 1 Hz to about 50 Hz, and producing condensed output information indicating presence and severity of a cerebral white-matter neural injury.

25. The method of claim 24 further comprising analyzing an intensity of the EEG signal within the range of about 2 Hz to about 20 Hz.

26. The method of claim 25 further comprising repeatedly determining a numerical value for the upper spectral edge of the frequency distribution of the intensity within the EEG signal for each of a series of time intervals, storing a corresponding series of spectral edge values, and presenting the series of spectral edge values in a graphical form.

27. The method of claim 24 further comprising comparing the analyzed data with stored reference spectral edge values and neurological outcome information from subjects of a similar age range and forecasting an outcome useful for managing the subject.

28. The method of claim 27 further comprising the step of rating a subject as follows: if the spectral edge value is below a first, lowest value, there is a likelihood of severe cerebral white-matter neural injury (WMI); if the spectral edge value is between the first and a second value, there is a likelihood of moderate WMI; if the spectral edge value is between the second and a third value, there is a likelihood of mild WMI; and if the spectral edge value is above the third value, there is little likelihood of WMI.

29. The method of claim 28 where the first value is 6 Hz; the second value is 8 Hz, and the third value is 10 Hz.

30. The method of claim 27 further comprising the step of rating a subject as follows: if the spectral edge value, there is a high likelihood of cerebral white-matter neural injury; if the spectral edge value is between the first and a second value, the subject requires further monitoring; and if the spectral edge is above the second value, there is a high likelihood that no white-matter injury exists.

31. The method of claim 30 where the first value is 8 Hz and the second value is 10 Hz.

32. The method of claim 24 where the subject is a pre-term infant.

33. The method of claim 24 where the EEG signal is acquired from electrodes placed on the subject's head over the parasagittal region/fronto-parietal-occipital cortex.

34. An apparatus for processing an electroencephalogram (EEG) signal from a subject to assist in management of possible cerebral white-matter neural injury in the subject, comprising:
(a) apparatus to acquire at least one channel of an EEG signal from the subject over a period of time, and
(b) computing apparatus programmed to analyze the frequency distribution of the intensity of the EEG signal so acquired, from within a range of from 1 Hz to 50 Hz, and to produce a numerical value for the upper spectral edge of the frequency distribution of the intensity of the EEG signals.

35. The apparatus of claim 34 further comprising apparatus to determine the spectral edge for each of a series of time intervals, to store a corresponding series of spectral edge values, and to include the series of spectral edge values on a display, thereby to enable forecasting of an outcome of cerebral white-matter neural injury in the subject.

36. The apparatus of claim 35 further comprising apparatus to determine, within the range of 1 Hz to 35 Hz, the upper spectral edge below which about 95% of the EEG intensity occurs.

37. The apparatus of claim 36 further comprising apparatus to provide a comparison of the determined upper spectral edge with stored EEG upper spectral edge and associated neurological outcome information from previous cases, thereby to enable forecasting of an outcome of cerebral white-matter neural injury in the subject.

38. The apparatus of claim 37 further comprising apparatus to acquire a plurality of channels of EEG signals, so that spectral edge recordings are made from a plurality of positions on the head of the subject, thereby to improve confidence in forecasting an outcome of cerebral white-matter neural injury in the subject.

39. A program embodied on a computer readable medium in combination with the apparatus of claim 38, the program comprising a routine to display comparable portions of both a current record and a previously collected record thereby permitting a comparison of the current record with stored information derived from the EEG and neurological outcome information from previous cases, thereby enabling prediction of an outcome of cerebral white-matter neural injury in the subject.

40. The apparatus of claim 36 further comprising apparatus programmed to eliminate an artifact in output information by action of at least one event-responsive filtering procedure to delete from the output information data likely to be in error.

41. The apparatus of claim 40 where the event-responsive filtering procedure is a signal interruption procedure that rejects the determined upper spectral edge during detection of a condition within the EEG signal selected from abnormally low signal amplitude, abnormally high signal amplitude, a signal indicating a seizure in the subject, a signal indicative of sleep in the subject, and a signal indicative of a presence of electrical interference.

42. A program embodied on a computer readable medium in combination with the apparatus of claim 40, the program comprising a routine to display an annotated image of a head to indicate a suitable position for the placement of EEG electrodes.

43. A program embodied on a computer readable medium in combination with the apparatus of claim 41, the program comprising at least one routine to accept data representing a digitized EEG signal and filter the data to exclude data likely to be in error, thereby facilitating prediction of the outcome of cerebral white-matter neural injury in the subject.

44. The program embodied on a computer readable medium of claim 43 further comprising at least one routine to receive information and to act on the data in response to the information to minimize the effect of an artifact.

45. The program embodied on a computer readable medium of claim 43 further comprising at least one routine to analyze the incoming data to establish the likely presence of an artifact, and, if the likely presence of an artifact is established, to output and advisory message to an operator to cause the removal of the artifact.

46. The apparatus of claim 40 further comprising a movement sensor and where the event-responsive filtering procedure is a signal interruption procedure that rejects the determined upper spectral edge during detection of movement.

47. The apparatus of claim 40 further comprising an electrode impedance detector and where the event-responsive filtering procedure is a signal interruption procedure that rejects the determined upper spectral edge during detection of an incorrect electrode impedance.

48. The apparatus of claim 40 further comprising an electrode identification detector and where the event-responsive filtering procedure is a signal interruption procedure that rejects the determined upper spectral edge during detection of an inappropriate electrode.

49. The apparatus of claim 40 further comprising an input apparatus through which an operator can input information describing the developmental status of the subject and apparatus programmed to make alterations to filter parameters in accordance with known neurophysiological parameters of subjects of that developmental status.

50. The apparatus of claim 40 further comprising apparatus for issuing an appropriate advisory message to an operator for the operator to cause removal of the artifact.

51. The apparatus of claim 35 further comprising apparatus to determine, between 2 Hz and 20 Hz, the upper spectral edge below which about 90% of the EEG intensity occurs.

52. A method for using the apparatus of claim 35 including screening at least one subject from time to time by using the apparatus to define the characteristics of the EEG of the subject to determine whether the subject being screened is at risk of cerebral white-matter neural injury to allow treatment and or forecasts of likely outcomes to be made accordingly.

53. A method for using the apparatus of claim 35 including continuously monitoring at least one subject by using the apparatus to define and follow the characteristics of the EEG of the subject in order to determine the presence and extent of cerebral white-matter neural injury to allow effectiveness of any treatment of the subject to be monitored and/or to allow a forecast of likely outcome to be made.

54. A program embodied on a computer readable medium in combination with the apparatus of claim 34, the program comprising a routine to accept data representing a digitized EEG signal and provide an output representing a numerical value for the upper spectral edge of the frequency distribution of the intensity within the EEG signal.

55. A method for predicting cerebral white-matter neural injury in a subject comprising:
   (a) acquiring, over a period of time, an EEG signal from the subject,
   (b) analyzing a frequency distribution of the signal within the range of about 1 Hz to about 50 Hz,
   (c) determining a spectral edge of said frequency distribution; and
   (d) comparing the spectral edge determined in step (c) with a spectral edge determined from one or more subjects without cerebral white-matter neural injury to predict cerebral white-matter neural injury.

56. The method of claim 55 further comprising analyzing an intensity of the EEG signal within the range of about 2 Hz to about 20 Hz.

57. The method of claim 45 further comprising repeatedly determining a numerical value for the upper spectral edge of the frequency distribution of the intensity within the EEG signal for each of a series of time intervals, storing a corresponding series of spectral edge values, and presenting the series of spectral edge values in a graphical form.

58. The method of claim 45 further comprising comparing the analyzed data with stored reference a spectral edge value and neurological outcome information from one or more subjects of a similar age range and forecasting an outcome useful for managing the subject.

59. The method of claim 58 further comprising the step of rating a subject as follows:
   (a) if the spectral edge value is below a first, lowest value, there is a likelihood of severe cerebral white-matter neural injury (WMI); if the spectral edge value is between the first and a second value, there is a likelihood of moderate WMI; if the spectral edge value is between the second and a third value, there is a likelihood of mild WMI; and if the spectral edge value is above the third value, there is little likelihood of WMI.

60. The method of claim 59 where the first value is 6 Hz; the second value is 8 Hz, and the third value is 10 Hz.

61. The method of claim 58 further comprising the step of rating a subject as follows: if the spectral edge value, there is a high likelihood of cerebral white-matter neural injury; if the spectral edge value is between the first and a second value, the subject requires further monitoring; and if the spectral edge is above the second value, there is a high likelihood that no white-matter injury exists.

62. The method of claim 61 where the first value is 8 Hz and the second value is 10 Hz.

63. The method of claim 55 where the subject is a pre-term infant.

64. The method of claim 55 where the EEG signal is acquired from electrodes placed on the subject's head over the parasagittal region/fronto-parietal-occipital cortex.

* * * * *